US007994127B2

(12) United States Patent
Sur et al.

(10) Patent No.: US 7,994,127 B2
(45) Date of Patent: Aug. 9, 2011

(54) TREATMENT OF RETT SYNDROME

(75) Inventors: Mriganka Sur, Cambridge, MA (US); Daniela Tropea, Cambridge, MA (US); Emanuela Giacometti, Cambridge, MA (US); Rudolf Jaenisch, Brookline, MA (US); Nathan R. Wilson, Cambridge, MA (US)

(73) Assignees: Massachusetts Institute of Technology, Cambridge, MA (US); Whitehead Institute of Biomedical Research, Cambridge, MA (US)

( * ) Notice: Subject to any disclaimer, the term of this patent is extended or adjusted under 35 U.S.C. 154(b) by 0 days.

(21) Appl. No.: 12/134,707

(22) Filed: Jun. 6, 2008

(65) Prior Publication Data
US 2009/0099077 A1 Apr. 16, 2009

Related U.S. Application Data

(60) Provisional application No. 60/933,738, filed on Jun. 8, 2007.

(51) Int. Cl.
*A61K 38/30* (2006.01)
(52) U.S. Cl. .................. 514/8.6; 514/21.9
(58) Field of Classification Search .............. None
See application file for complete search history.

(56) References Cited

U.S. PATENT DOCUMENTS

| | | | |
|---|---|---|---|
| 4,411,890 A | 10/1983 | Momany et al. | |
| 5,093,317 A * | 3/1992 | Lewis et al. | 514/12 |
| 5,420,112 A | 5/1995 | Lewis et al. | |
| 5,446,024 A | 8/1995 | Builder et al. | |
| 5,565,428 A | 10/1996 | Clark et al. | |
| 5,714,460 A | 2/1998 | Gluckman et al. | |
| 6,331,414 B1 | 12/2001 | Lee et al. | |
| 6,559,150 B2 | 5/2003 | Carpino et al. | |
| 7,041,314 B2 | 5/2006 | Abood et al. | |
| 7,304,029 B1 | 12/2007 | Scheepens et al. | |
| 2002/0013277 A1 | 1/2002 | Gluckman et al. | |
| 2002/0160384 A1 | 10/2002 | Ashkenazi et al. | |
| 2002/0160955 A1 | 10/2002 | Dubaquie et al. | |
| 2002/0165155 A1 | 11/2002 | Schaffer et al. | |
| 2003/0055004 A1 | 3/2003 | Abood et al. | |
| 2005/0059598 A1 | 3/2005 | Clark et al. | |
| 2006/0064249 A1 | 3/2006 | Clark et al. | |
| 2006/0100287 A1 | 5/2006 | Okajima et al. | |
| 2006/0217295 A1 | 9/2006 | Harris et al. | |
| 2007/0224165 A1 | 9/2007 | Guan et al. | |
| 2008/0145335 A1 | 6/2008 | Brimble et al. | |

FOREIGN PATENT DOCUMENTS

| | | |
|---|---|---|
| EP | 0 366 638 A2 | 5/1990 |
| WO | WO 89/07110 A1 | 8/1989 |
| WO | WO 89/07111 A1 | 8/1989 |
| WO | WO 02/16408 A2 | 2/2002 |
| WO | WO 02/056873 A2 | 7/2002 |
| WO | WO 02/057241 A1 | 7/2002 |
| WO | WO 2005/009394 A2 | 2/2005 |
| WO | WO 2006/130769 A2 | 12/2006 |
| WO | WO 2007/120847 A2 | 10/2007 |

OTHER PUBLICATIONS

Xing et al. (Exp. Neurology 205: 222-229, 2007).*
Gemelli et al. (Biol. Psychiatry 59: 468-476, 2006).*
Huppke et al. Acta Paediatr. 90: 1257-1261, 2001.*
Tropea et al. PNAS 106(6): 2029-2034, 2009.*
Kaufmann et al. Brain & Development 27: S77-S87, 2005.*
Aberg et al., Peripheral infusion of IGf-I selectively induces neurogenesis in the adult rat hippocampus. J Neurosci. Apr. 15, 2000;20(8):2896-903.
Bondy, Transient IGF-I gene expression during the maturation of functionally related central projection neurons. J Neurosci. Nov. 1991;11(11):3442-55.
Chahrour et al., The story of Rett syndrome: from clinic to neurobiology. Neuron. Nov. 8, 2007;56(3):422-37. Review.
Chang et al., The disease progression of Mecp2 mutant mice is affected by the level of BDNF expression. Neuron. Feb. 2, 2006;49(3):341-8.
Chao et al., MeCP2 controls excitatory synaptic strength by regulating glutamatergic synapse number. Neuron. Oct. 4, 2007;56(1):58-65.
Dani et al., Reduced cortical activity due to a shift in the balance between excitation and inhibition in a mouse model of Rett syndrome. Proc Natl Acad Sci U S A. Aug. 30, 2005;102(35):12560-5. Epub Aug 22, 2005.
Doré et al., Rediscovering an old friend, IGF-I: potential use in the treatment of neurodegenerative diseases. Trends Neurosci. Aug. 1997;20(8):326-31. Review.
Giacometti et al., Partial rescue of MeCP2 deficiency by postnatal activation of MeCP2. Proc Natl Acad Sci U S A. Feb. 6, 2007;104(6):1931-6. Epub Jan. 31, 2007.
Gordon et al., Experience-dependent plasticity of binocular responses in the primary visual cortex of the mouse. J Neurosci. May 15, 1996;16(10):3274-86.
Nelson et al., MeCP2-dependent transcriptional repression regulates excitatory neurotransmission. Curr Biol. Apr. 4, 2006;16(7):710-6.
Ramsey et al., Functional characterization of des-IGF-1 action at excitatory synapses in the CA1 region of rat hippocampus. J Neurophysiol. Jul. 2005;94(1):247-54.
Riikonen et al., Cerebrospinal fluid insulin-like growth factors IGF-1 and IGF-2 in infantile autism. Dev Med Child Neurol. Sep. 2006;48(9):751-5.
Riikonen, Insulin-like growth factor delivery across the blood-brain barrier. Potential use of IGF-1 as a drug in child neurology. Chemotherapy. 2006;52(6):279-81. Epub Sep 27, 2006.
Shahbazian et al., Mice with truncated MeCP2 recapitulate many Rett syndrome features and display hyperacetylation of histone H3. Neuron. Jul. 18, 2002;35(2):243-54.
Shahbazian et al., Insight into Rett syndrome: MeCP2 levels display tissue- and cell-specific differences and correlate with neuronal maturation. Hum Mol Genet. Jan. 15, 2002;11(2):115-24.
Tudor et al., Transcriptional profiling of a mouse model for Rett syndrome reveals subtle transcriptional changes in the brain. Proc Natl Acad Sci U S A. Nov. 26, 2002;99(24):15536-41. Epub Nov. 13, 2002.

(Continued)

Primary Examiner — Christine J Saoud
(74) Attorney, Agent, or Firm — Wolf, Greenfield & Sacks, P.C.

(57) ABSTRACT

The invention relates to methods for treatment of Rett Syndrome and other disorders of synaptic function and maturation using IGF1, (1-3)IGF-1, (1-3)IGF-1 analog(s) and/or related therapeutic molecules.

20 Claims, 8 Drawing Sheets

OTHER PUBLICATIONS

Zheng et al., Comparative signaling pathways of insulin-like growth factor-1 and brain-derived neurotrophic factor in hippocampal neurons and the role of the PI3 kinase pathway in cell survival. J Neurochem. May 2004;89(4):844-52.

Aberg et al., IGF-I has a direct proliferative effect in adult hippocampal progenitor cells. Mol Cell Neurosci. Sep. 2003;24(1):23-40.

Acampa et al., Cardiac disease and Rett syndrome. Arch Dis Child. May 2006;91(5):440-443. Review.

Amir et al., Rett syndrome is caused by mutations in X-linked MECP2, encoding methyl-CpG-binding protein 2. Nat Genet. Oct. 1999;23(2):185-188.

Ankersen et al., Demonstration of the strength of focused combinatorial libraries in SAR optimization of growth hormone secretagogues. Eur J Med Chem. Oct. 1999;34(10):783-790.

Ankersen et al., Growth hormone secretagogues derived from NN703 with hydrazidesas c-terminal. Eur J Med Chem. May 2000;35(5):487-497.

Baker et al., Central penetration and stability of N-terminal tripeptide of insulin-like growth factor-I, glycine-proline-glutamate in adult rat. Neuropeptides. Apr. 2005;39(2):81-7. Epub Jan. 28, 2005.

Ciucci et al., Insulin-like growth factor 1 (IGF-1) mediates the effects of enriched environment (EE) on visual cortical development. PLoS One. May 30, 2007;2(5):e475.

Chen et al., Deficiency of methyl-CpG binding protein-2 in CNS neurons results in a Rett-like phenotype in mice. Nat Genet. Mar. 2001;27(3):327-31.

Chen et al., Derepression of BDNF transcription involves calcium-dependent phosphorylation of MeCP2. Science. Oct. 31, 2003;302(5646):885-9.

Cohen et al., Expression of MeCP2 in olfactory receptor neurons is developmentally regulated and occurs before synaptogenesis. Mol Cell Neurosci. Apr. 2003;22(4):417-429.

El-Husseini et al., PSD-95 involvement in maturation of excitatory synapses. Science. Nov. 17, 2000;290(5495):1364-1368.

Guan et al., Neuroprotective effects of the N-terminal tripeptide of insulin-like growth factor-1, glycine-proline-glutamate (GPE) following intravenous infusion in hypoxic-ischemic adult rats. Neuropharmacology. Nov. 2004;47(6):892-903.

Guy et al., Reversal of neurological defects in a mouse model of Rett syndrome. Science. Feb. 23, 2007 23;315(5815):1143-7. Epub Feb. 8, 2007.

Guy et al., A mouse Mecp2-null mutation causes neurological symptoms that mimic Rett syndrome. Nat Genet. Mar. 2001;27(3):322-326.

Hofer et al., Prior experience enhances plasticity in adult visual cortex. Nat Neurosci. Jan. 2006;9(1):127-32. Epub Dec. 4, 2005.

Itoh et al., Methyl CpG-binding protein 2 (a mutation of which causes Rett syndrome) directly regulates insulin-like growth factor binding protein 3 in mouse and human brains. J Neuropathol Exp Neurol. Feb. 2007;66(2):117-23.

Johnston et al., Neurobiology of Rett syndrome: a genetic disorder of synapse development. Brain Dev. Dec. 2001;23 Suppl 1:S206-S213. Review.

Julu et al., Characterisation of breathing and associated central autonomic dysfunction in the Rett disorder. Arch Dis Child. Jul. 2001;85(1):29-37.

Kaufmann et al., Abnormalities in neuronal maturation in Rett syndrome neocortex: preliminary molecular correlates. Eur Child Adolesc Psychiatry. 1997;6 Suppl 1:75-7. Erratum in: Eur Child Adolesc Psychiatry Jun. 1998;7(2):124.

Langer, New methods of drug delivery. Science. Sep. 28, 1990;249(4976):1527-1533. Review.

Lee et al., Insulin stimulates postsynaptic density-95 protein translation via the phosphoinositide 3-kinase-Akt-mammalian target of rapamycin signaling pathway. J Biol Chem. May 6, 2005;280(18):18543-50. Epub Mar. 8, 2005.

Liu et al., Mice carrying null mutations of the genes encoding insulin-like growth factor I (Igf-1) and type 1 IGF receptor (Igf1r). Cell. Oct. 8, 1993;75(1):59-72.

Lupien et al., Systemic insulin-like growth factor-I administration prevents cognitive impairment in diabetic rats, and brain IGF regulates learning/memory in normal adult rats. J Neurosci Res. Nov. 15, 2003;74(4):512-523.

Nan et al., Transcriptional repression by the methyl-CpG-binding protein MeCP2 involves a histone deacetylase complex. Nature. May 28, 1998;393(6683):386-389.

Rudman et al., Effects of human growth hormone in men over 60 years old. N. Engl J Med. Jul. 5, 1990;323(1):1-6.

Saatman et al., Insulin-like growth factor-1 (IGF-1) improves both neurological motor and cognitive outcome following experimental brain injury. Exp Neurol. Oct. 1997;147(2):418-27.

Saura et al., Neuroprotective effects of Gly-Pro-Glu, the N-terminal tripeptide of IGF-1, in the hippocampus in vitro. Neuroreport. Jan. 18, 1999;10(1):161-164.

Schuman, Neurotrophin regulation of synaptic transmission. Curr Opin Neurobiol. Feb. 1999;9(1):105-109. Review.

Seyler et al., Effect of growth hormone secretagogue LY444711 on IGF-1, growth hormone, and cortisol levels in beagle dogs after one and seven daily oral doses. Drug Devel Res. Apr. 2000;49(4):260-265.

Sizonenko et al., Neuroprotective effects of the N-terminal tripeptide of IGF-1, glycine-proline-glutamate, in the immature rat brain after hypoxic-ischemic injury. Brain Res. Dec. 13, 2001;922(1):42-50.

Smith et al., Experience-dependent binocular competition in the visual cortex begins at eye opening. Nat Neurosci. Mar. 2007;10(3):370-5. Epub Feb. 11, 2007.

Tropea et al., Gene expression changes and molecular pathways mediating activity-dependent plasticity in visual cortex. Nat Neurosci. May 2006;9(5):660-8. Epub Apr. 23, 2006.

Yoshii et al., BDNF induces transport of PSD-95 to dendrites through PI3K-AKT signaling after NMDA receptor activation. Nat Neurosci. Jun. 2007;10(6):702-711. Epub May 21, 2007.

* cited by examiner

TREATMENT OF RETT SYNDROME

RELATED APPLICATION

This application claims the benefit under 35 U.S.C. §119 (e) of U.S. provisional application 60/933,738, filed Jun. 8, 2007, the entire disclosure of which is incorporated herein by reference.

GOVERNMENT SUPPORT

This invention was made in part with Government support from the National Institutes of Health (Grants RO1-CA087869 and RO1-HD045022). The Government has certain rights in the invention.

FIELD OF THE INVENTION

The invention relates to methods for treatment of Rett Syndrome and other disorders of synaptic function and maturation.

BACKGROUND OF THE INVENTION

Rett Syndrome (RTT) is a developmental disorder linked to mutations in the X chromosome gene methyl CpG-binding protein 2 (MeCP2). MeCP2 codes for a protein that regulates transcription. It forms a transcription repressor complex that binds to methylated gene sequences, and induces chromatin condensation.

Patients with Rett Syndrome, who are almost exclusively females, show distinctive hand movements, slowed brain growth, regression of language and motor skills, seizures, cognitive impairment and mental retardation. Cortical structure is relatively preserved, but dendritic structure is altered and dendritic spines appear structurally immature.

Mouse models of Rett Syndrome have been made (Chen et al., Nat Genet. 27 (3):327-31, 2001; Guy et al., Nat Genet. 27 (3):322-6, 2001; Shahbazian et al., Neuron 35 (2):243-54, 2002). MeCP2 knockout (KO) mice show movement and respiratory phenotype, smaller pyramidal neurons, and electrophysiological abnormalities suggestive of synaptic and neuronal immaturity. A truncating mutation of MeCP2 leads to motor and social dysfunction, alterations in synaptic plasticity and memory.

Restoration of MeCP2 levels in a conditional MeCP2 KO mouse model restores movement function (Guy et al., Science 315 (5815):1143-7, 2007). Enhanced BDNF expression in KO mice reverses the movement and electrophysiological phenotype (Chang et al., Neuron 49 (3):341-8, 2006). These and other data suggest that synapses remain in an immature state in the mouse models, and appropriate treatments even late in development can re-establish function.

SUMMARY OF THE INVENTION

There is a strong incentive to identify new and/or better treatment options for Rett syndrome and other disorders that have synaptic and neuronal immaturity or alterations in synaptic plasticity, such as autism spectrum disorders.

Working under a hypothesis that genes and molecules that enhance synapse maturation might restore synaptic and behavioral function in MeCP2 KO mice, the applicants have determined that insulin-like growth factor (IGF1) or (1-3) IGF-1 (also known as glycyl-L-prolyl-L-glutamic acid, glycine-proline-glutamate and GPE), a peptide fragment of IGF1, unexpectedly are viable candidates for restoring function in MeCP2 KO mice and for human RTT therapeutics. Both of these molecules, and other analogous molecules such as (1-3)IGF-1 analogs that also can be used in the invention, cross the blood-brain barrier, and thus can be administered systemically as small molecule therapeutics for RTT and other disorders. In contrast, larger molecule such as brain-derived neurotrophic factor (BDNF) and most other synaptic plasticity molecules do not cross the blood-brain barrier, and therefore would require direct brain infusion, which is not practical in humans.

According to one aspect of the invention, methods for treating Rett Syndrome are provided. The methods include administering to a subject in need of such treatment an effective amount of insulin-like growth factor (IGF1), (1-3)IGF-1, and/or a (1-3)IGF-1 analog to treat the subject.

In some embodiments, IGF1 is administered. Preferably the IGF1 is recombinant IGF1 or human IGF1. In preferred embodiments, the dose of IGF1 administered is about 0.1-10 mg/kg/day, more preferably about 0.1-2 mg/kg/day.

In other embodiments, (1-3)IGF-1 is administered. In preferred embodiments, the dose of (1-3)IGF-1 administered is about 0.1-100 mg/kg/day, more preferably about 6-20 mg/kg/day.

In still other embodiments, a (1-3)IGF-1 analog is administered. Preferably the (1-3)IGF-1 analog is Gly-Pro; Pro-Glu; a (1-3)IGF-1 substitution analog wherein the Gly of Gly-Pro-Glu is replaced by any of Ala, Ser, Thr, or Pro or wherein the Pro of Gly-Pro-Glu is replaced by any of Ala, Ser, Thr, or Gly or wherein the Glu of Gly-Pro-Glu is replaced by any of Asn, Asp, or Gln; a (1-3)IGF-1 amide, a (1-3)IGF-1 stearate, a (1-3)IGF-1 analog having one or two D-amino acids, or a (1-3)IGF-1 analog having one or two non-hydrolyzable peptide bonds.

In additional embodiments, a related therapeutic molecule is administered. Preferably the related therapeutic molecule is an IGF1 secretagogue, a growth hormone or precursor, a growth hormone secretagogue, a growth hormone releasing peptide, or a growth hormone releasing hormone or analog.

In preferred embodiments of the methods, the subject is a human.

In certain embodiments of the methods, the IGF1, (1-3) IGF-1 and/or (1-3)IGF-1 analog is administered orally, intravenously, intramuscularly, intranasally, intraperitoneally, subcutaneously, or intrathecally.

The IGF1, (1-3)IGF-1 and/or (1-3)IGF-1 analog can be administered after diagnosis of Rett syndrome, or can be administered prophylactically before diagnosis of Rett syndrome.

In further embodiments, the subject is free of symptoms otherwise calling for treatment with the IGF1, (1-3)IGF-1 or (1-3)IGF-1 analog.

In further embodiments, the methods also include first testing the subject for a mutation in a gene coding for methyl CpG-binding protein 2 (MeCP2).

In some embodiments, the methods also include administering to the subject a second therapeutic, wherein the second therapeutic is tPA, BDNF, a molecule that regulates inhibition such as a benzodiazepine, or a molecule that is a neurotransmitter agonist, antagonist or analog, and wherein the second therapeutic and the IGF1, (1-3)IGF-1, (1-3)IGF1 analog(s) and/or related therapeutic molecules are administered in a combined amount effective to treat the subject.

In the foregoing methods, the amount of IGF1, (1-3)IGF-1, (1-3)IGF-1 analog(s) and/or related therapeutic molecules is effective to restore synaptic function and/or maturation, consolidate synapses and/or regulate neuronal plasticity.

According to another aspect of the invention, methods for treating a disorder of synaptic function and/or maturation in a subject are provided. The methods include administering to a subject in need of such treatment an effective amount of insulin-like growth factor (IGF1), glycyl-L-prolyl-L-glutamic acid ((1-3)IGF-1), and/or a (1-3)IGF-1 analog to treat the subject.

In some embodiments, IGF1 is administered. Preferably the IGF1 is recombinant IGF1 or human IGF1. In preferred embodiments, the dose of IGF1 administered is about 0.1-10 mg/kg/day, more preferably about 0.1-2 mg/kg/day.

In other embodiments, (1-3)IGF-1 is administered. In preferred embodiments, the dose of (1-3)IGF-1 administered is about 0.1-100 mg/kg/day, more preferably about 6-20 mg/kg/day.

In still other embodiments, a (1-3)IGF-1 analog is administered. Preferably the (1-3)IGF-1 analog is Gly-Pro; Pro-Glu; a (1-3)IGF-1 substitution analog wherein the Gly of Gly-Pro-Glu is replaced by any of Ala, Ser, Thr, or Pro or wherein the Pro of Gly-Pro-Glu is replaced by any of Ala, Ser, Thr, or Gly or wherein the Glu of Gly-Pro-Glu is replaced by any of Asn, Asp, or Gln; a (1-3)IGF-1 amide, a (1-3)IGF-1 stearate, a (1-3)IGF-1 analog having one or two D-amino acids, or a (1-3)IGF-1 analog having one or two non-hydrolyzable peptide bonds.

In additional embodiments, a related therapeutic molecule is administered. Preferably the related therapeutic molecule is an IGF1 secretagogue, a growth hormone or precursor, a growth hormone secretagogue, a growth hormone releasing peptide, or a growth hormone releasing hormone or analog.

In preferred embodiments of the methods, the subject is a human.

In certain embodiments of the methods, the IGF1, (1-3)IGF-1 and/or (1-3)IGF-1 analog is administered orally, intravenously, intramuscularly, intranasally, intraperitoneally, subcutaneously, or intrathecally.

The IGF1, (1-3)IGF-1 and/or (1-3)IGF-1 analog can be administered after diagnosis of the disorder, or can be administered prophylactically before diagnosis of the disorder.

In preferred embodiments, the disorder is autism, autism spectrum disorder, Angelmann's Syndrome, tuberous sclerosis, Fragile X syndrome, schizophrenia, depression, neurodegenerative disorders including Parkinson's disease, Huntington's disease and Alzheimer's disease, stroke or trauma.

In further embodiments, the subject is free of symptoms otherwise calling for treatment with the IGF1, (1-3)IGF-1 or (1-3)IGF-1 analog.

In some embodiments, the methods also include first testing the subject for a mutation in a gene that is a genetic basis for the disorder or a gene that is a target of or downstream of such a gene.

In other embodiments, the methods also include administering to the subject a second therapeutic, wherein the second therapeutic is tPA, BDNF, a molecule that regulates inhibition such as a benzodiazepine, and/or a molecule that is a neurotransmitter agonist, antagonist or analog. In such embodiments, the second therapeutic and the IGF1, (1-3)IGF-1 and/or (1-3)IGF1 analog are administered in a combined amount effective to treat the subject.

In the foregoing methods, the amount of IGF1, (1-3)IGF-1 and/or (1-3)IGF-1 analog is effective to restore synaptic function and/or maturation, consolidate synapses and/or regulate neuronal plasticity.

According to a third aspect of the invention, methods for increasing synaptic maturation are provided. The methods include contacting one or more neurons comprising one or more synapses with an amount of IGF1, (1-3)IGF-1, and/or a (1-3)IGF-1 analog effective to increase the maturation of the one or more synapses of the one or more neurons.

In some embodiments, the one or more neurons are contacted with IGF1. Preferably the IGF1 is recombinant IGF1 or human IGF1.

In other embodiments, the one or more neurons are contacted with (1-3)IGF-1 or a (1-3)IGF-1 analog. Preferably the (1-3)IGF-1 analog is Gly-Pro; Pro-Glu; a (1-3)IGF-1 substitution analog wherein the Gly of Gly-Pro-Glu is replaced by any of Ala, Ser, Thr, or Pro or wherein the Pro of Gly-Pro-Glu is replaced by any of Ala, Ser, Thr, or Gly or wherein the Glu of Gly-Pro-Glu is replaced by any of Asn, Asp, or Gln; a (1-3)IGF-1 amide, a (1-3)IGF-1 stearate, a (1-3)IGF-1 analog having one or two D-amino acids, or a (1-3)IGF-1 analog having one or two non-hydrolyzable peptide bonds.

In additional embodiments, a related therapeutic molecule is administered. Preferably the related therapeutic molecule is an IGF1 secretagogue, a growth hormone or precursor, a growth hormone secretagogue, a growth hormone releasing peptide, or a growth hormone releasing hormone or analog.

In preferred embodiments, the one or more neurons are human neurons.

In certain embodiments, the one or more neurons are contacted in vitro. In other embodiments, the one or more neurons are contacted in vivo. Preferably the contacting in vivo is performed by administering the IGF1, (1-3)IGF-1 and/or (1-3)IGF-1 analog to a subject. Preferably the IGF1, (1-3)IGF-1 and/or (1-3)IGF-1 analog is administered orally, intravenously, intramuscularly, intranasally, intraperitoneally, subcutaneously, or intrathecally.

Other related therapeutic molecules that can be used in a similar manner to treat the disorders as described herein include IGF1 secretagogues, growth hormones or precursors, growth hormone secretagogues, growth hormone releasing peptides, growth hormone releasing hormone and its analogs.

The treatment methods described herein also can include administering molecules that upregulate or enhance inhibition, such as benzodiazepines or others known to the person of skill in the art. The molecules that upregulate or enhance inhibition can be used alone or in combination with IGF1, (1-3)IGF-1 and/or (1-3)IGF-1 analog, etc, as described herein.

These and other aspects of the invention, as well as various advantages and utilities, will be more apparent with reference to the detailed description of the invention. Each aspect of the invention can encompass various embodiments as will be understood by the following description.

D. Distributions of intervals between EPSC events, reflecting EPSC frequency, are subtly but significantly modified between WT, and KO and KO-T groups.

Figure 2:
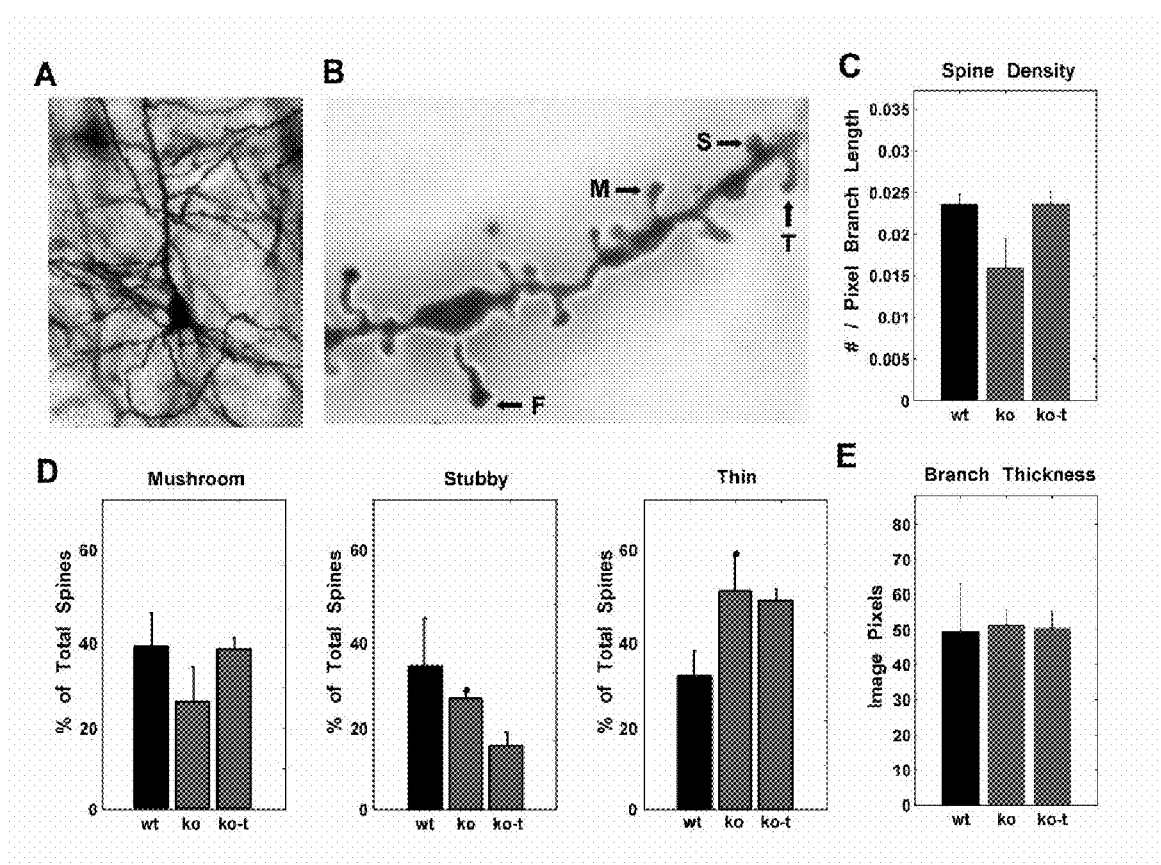

FIG. 2: Structural quantification of dendritic spine density and morphology.

A. Golgi staining of layer V pyramidal cells in motor cortex at P28 to enable the sparse labeling of neurons and spine morphology.

B. Confocal imaging at higher magnification (100×) enabled the clear depiction of different subclasses of dendritic spines, including filopodia (F), mushroom (M), stubby (S), and thin (T) class spines.

C. Pooling the number of these spines observed divided by the length of dendrite quantified per neuron yielded a trend in which neurons in knockout tissue exhibited reduced spine density compared to wild-type tissue. Knock-out tissue treated with (1-3)IGF1 exhibited spine densities more similar to wild-type values.

D. % of spines that were of a certain type for each treatment. Mushroom, or "mature" spines were reduced in the knockout compared to wild-type and knockout treated with (1-3)IGF1. There was also an over-representation of "thin" spines in the knockout that was not ameliorated by the treatment.

E. Average dendritic branch thickness did not vary between wild-type, knockout, and knockout treated with (1-3)IGF1.

Figure 3:
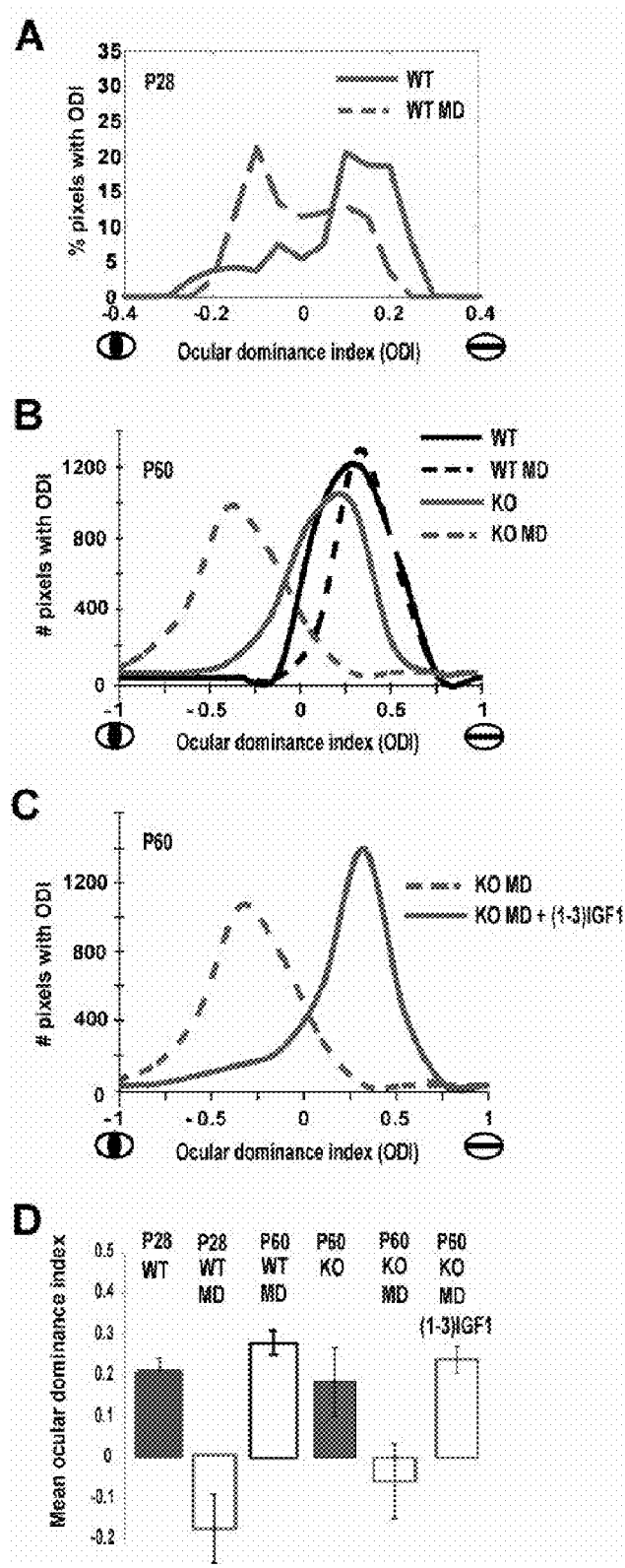

FIG. 3: Visual cortex plasticity in adult MeCP2 heterozygous mice is prevented by (1-3)IGF-1.

Ocular Dominance Index (ODI) distributions from individual young (P28) animals that either were not (WT) or were monocularly deprived of input for 4 days (WT MD), tracking relative activation of the cortical surface to stimulation delivered to each eye. Regions of analysis typically included 900-1300 pixels of cortical surface, and ODI values were derived from the optical signal intensity at each pixel driven by the two eyes (see Methods). The mean ODI value from each animal was used for the population analyses of part D.

A. In the young animals depicted here, a population ODI shift was observed in the WT MD animal (dashed line) in favor of the open eye compared to the non-deprived animal (solid line).

B. Adult wild type (black lines) and MeCP2 heterozygous mice (pink lines) either with monocular deprivation of the contralateral eye (MD, dashed lines) or without MD (continuous lines).

C. Adult MeCP2+/− mice following MD, either untreated (dashed purple line) or treated with (1-3)IGF-1 (red continuous line). Untreated mice show a shift in visual drive, measured by the ODI, away from the closed eye and towards the open eye, similar to developing animals (as in A)—demonstrating extended plasticity and indicating the persistence of immature synapses into adulthood. (1-3)IGF-1 treatment during the period of MD abolishes this plasticity, preserving an ocular dominance profile typical of adult animals (as in B).

D. Mean ODI values for developing wild type mice (~P28, left) and adult wild type mice (~P60, right). Positive ODI values indicate higher drive from the contralateral eye, and thus preserved organization, while negative values indicate higher drive from the ipsilateral eye, and thus altered circuitry. Wild type "wt", wild type after monocular deprivation "wt MD", MeCP2+/− "+/−", MeCP2+/− after monocular deprivation "+/−MD", and MeCP2+/− treated with (1-3)IGF-1 during monocular deprivation "+/−MD-t". After MD, visual cortex in wild type adult animals is still dominated by the contralateral eye while in adult MeCP2+/− mice there is severe reduction of contralateral eye drive and a shift of ODI towards the ipsilateral eye. Treatment with (1-3)IGF-1 in MeCP2+/− mice during MD prevents the ocular dominance shift towards the ipsilateral eye. The ODI values for P28 wild type animals were taken from Tropea et al. (Tropea et al., 2006).

Figure 4:
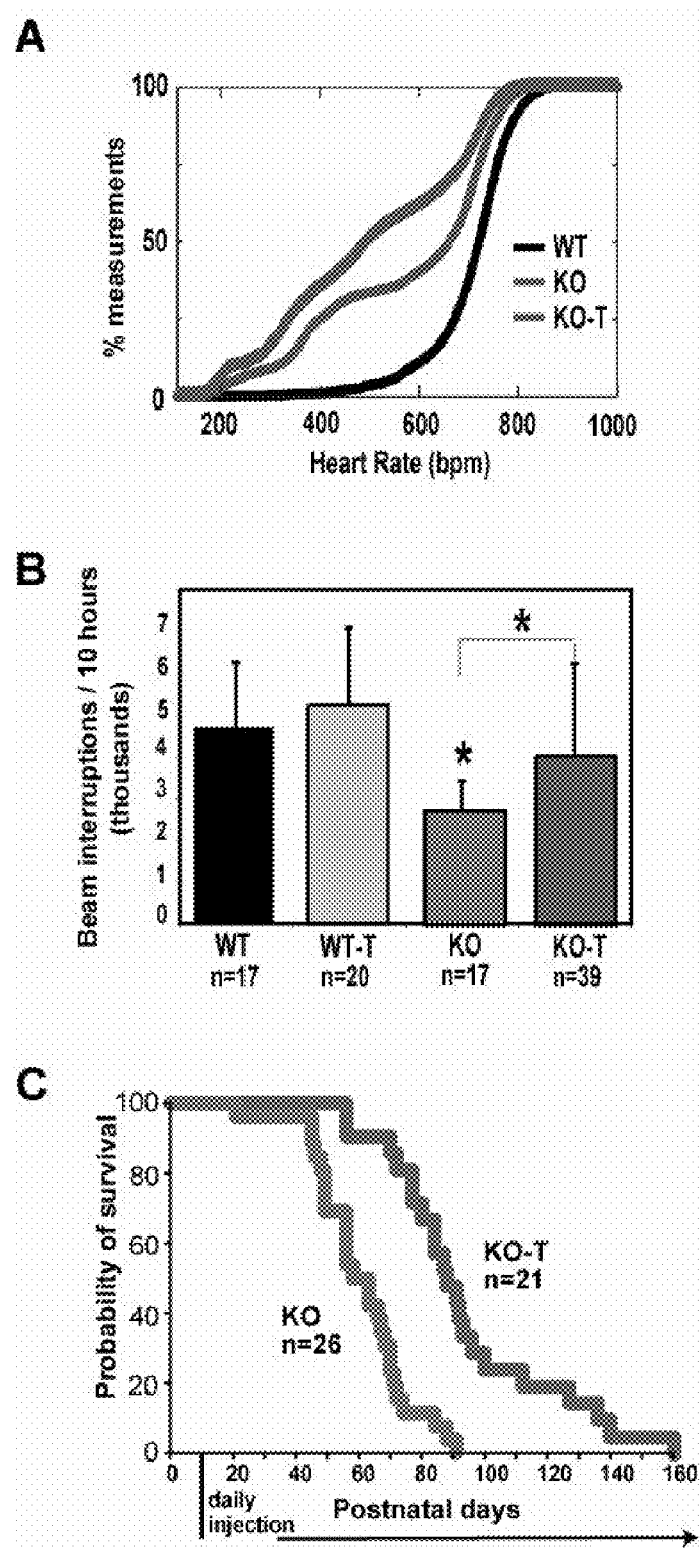

FIG. 4: Heart function, locomotor function, and survival are impaired in the MeCP2 knockout, and rescued following (1-3)IGF-1 treatment.

A. (1-3) IGF-1 reduces the frequency of bradycardia in MeCP2 null mice. Pooled heart rate distributions observed across mice from different treatments, in beats per minute (bpm). The Y axis depicts the percent of observations within an experimental group that exceed a given bpm value (X axis). Comparisons are between 8 week old animals (WT or KO), some of which received (1-3)IGF-1 treatment for 6 weeks (KO-T). The KO distribution (pink) was left-shifted compared to the wild-type distribution (black), indicating a significant reduction in the distribution of heart rates. The KO-T distribution (green) was in between the two curves, indicating a partial rescue of the KO phenotype towards a more normal wild-type distribution.

B. (1-3)IGF-1 treatment improves locomotor function in MeCP2 null mice. Baseline nocturnal activity was measured by placing animals in cages equipped with a movement detector (infrared beam). The Y axis shows the number of beam interruptions over 10 hours; each bar represents a different experimental group. Nocturnal activity was recorded weekly between 6 and 17 weeks of age—data from younger animals is also presented in FIG. 6. As expected, MeCP2 KO mice showed significantly less activity that wild type littermates. KO mice treated with (1-3)IGF-1, however, were more active than vehicle-treated KO animals (KO) but not as active as WT. Wild-type mice treated with (1-3)IGF-1 (WT-T) were not significantly more active than WT. "N"=number of animals per group.

C. (1-3)IGF-1 treated MeCP2 KO mice have longer life expectancy than vehicle treated controls. Kaplan-Meier survival curves for MeCP2−/y mice treated with vehicle (KO, red line) or (1-3)IGF-1 (KO-T, green line). The X axis shows the days after birth, and the Y axis shows the probability of survival. MeCP2−/y mice treated with (1-3)IGF-1 exhibited a significantly longer life expectancy that their vehicle treated littermates ($P=0.54*10^{-7}$, log rank test). MeCP2−/y mice were given daily IP injections of (1-3)IGF-1 (0.01 mg/g body weight/day) every day from 2 weeks of age onward. "n" is the number of mice per experimental group.

Figure 5:
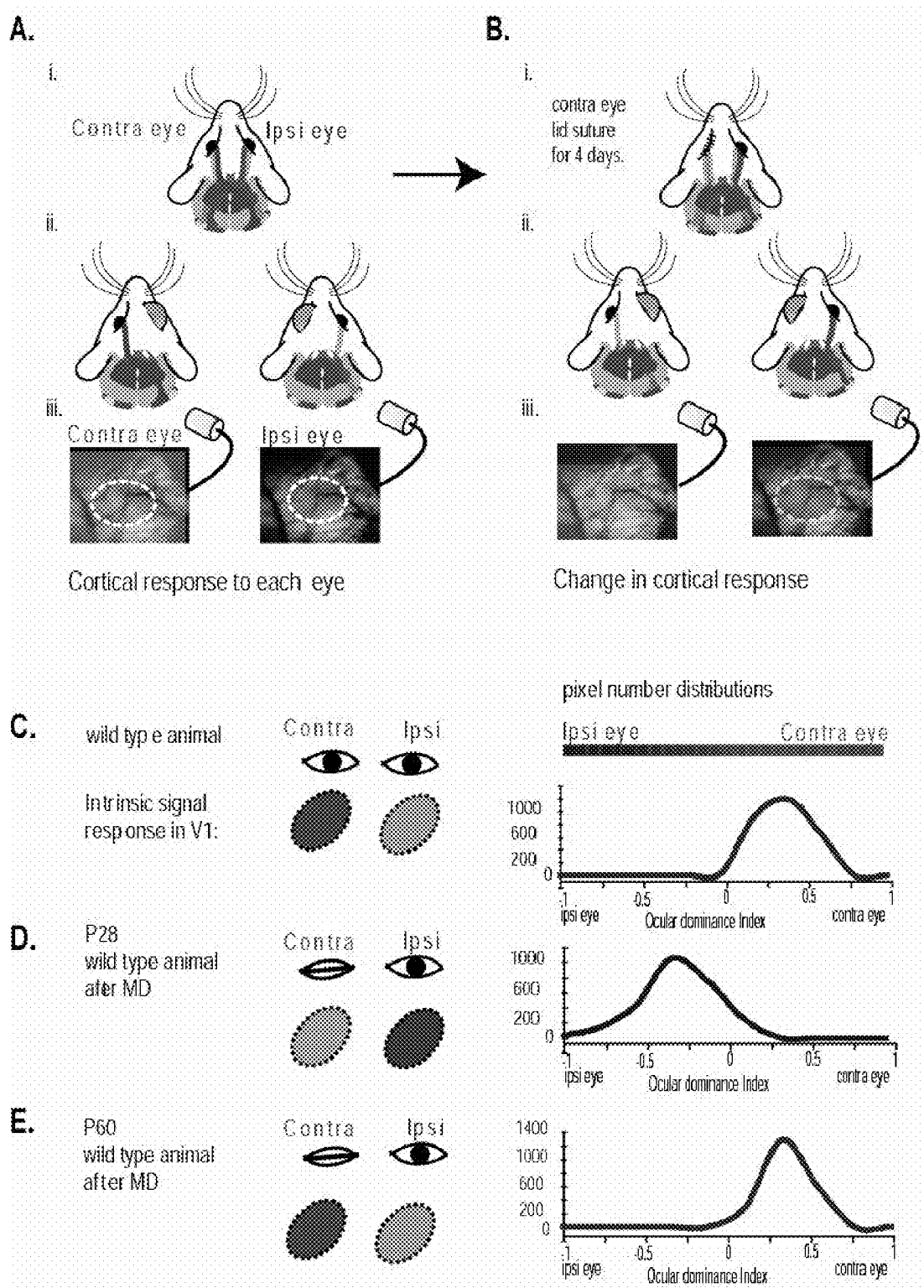

FIG. 5: Optical imaging of intrinsic signals to measure ocular dominance plasticity in visual cortex.

A. Optical imaging of intrinsic signals can be used to derive the strength of drive from each eye in primary visual cortex (V1).
  i. Schematic of visual pathway, showing inputs from each eye to V1.
  ii. Scheme of the optical imaging set-up. An anesthetized mouse is placed in front of a monitor displaying a periodic drifting bar stimulus. The skull surface is illuminated with red light (630 nm), and imaged with a CCD camera.
  iii. Blood vessel pattern in the binocular region of V1 (white circle) with representative optical signal levels when the contra eye (left, red signal) or the ipsilateral eye (right blue signal) is stimulated. The signal from the contralateral eye is stronger than the one from the ipsilateral eye.

B. Shift in ocular dominance after monocular deprivation in a young mouse.
  i. Monocular eye lid suture for 4 days.
  ii. After the lid suture is removed, each eye is stimulated in turn and visual responses in V1 are recorded.

iii. The short period of monocular deprivation causes a weakening of inputs from the deprived contralateral eye (red) and strengthening of inputs from the non-deprived ipsilateral eye (blue).

C-D. Schematic of signal intensity in the binocular region of V1 when each eye is stimulated under different conditions, in wild-type animals. Red and blue circles represent intensity of optical signal driven by the contralateral and ipsilateral eyes respectively. Ocular Dominance Index (ODI) distributions at right are derived from the relative strength of drive from each eye at each pixel. Three conditions are shown: a normal adult wild type mouse (C), a young mouse after 4 days of monocular deprivation (D) and an adult mouse after 4 days of MD. In a wild-type mouse, MD of the contralateral eye during development causes a shift in the signal intensity and ODI towards the open ipsilateral eye. Such plasticity is not seen after a similar period of MD in an adult animal.

Figure 6:
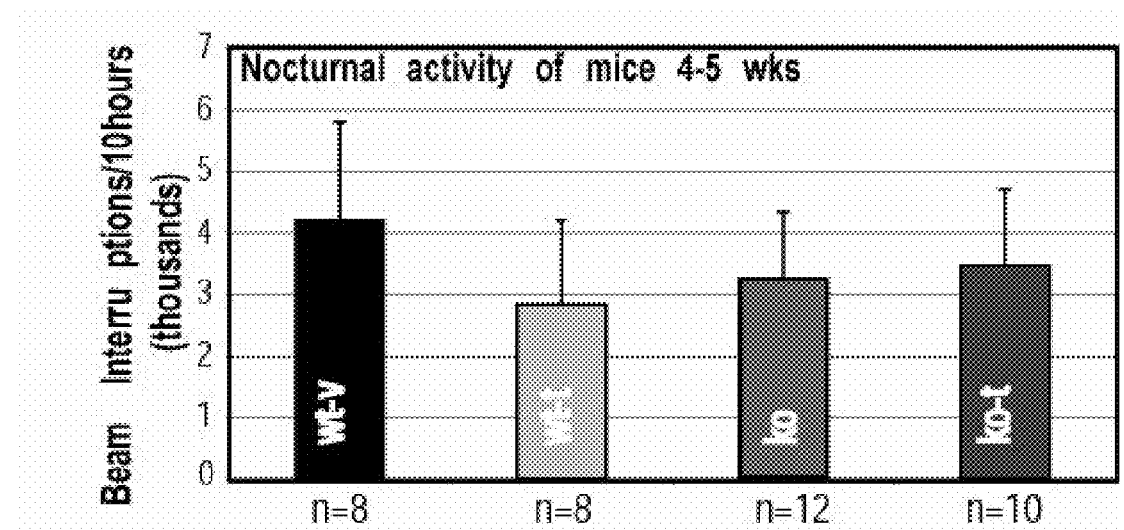

FIG. 6: (1-3)IGF-1 treatment and locomotor function in young MeCP2 null mice.

Baseline nocturnal activity was measured by placing animals in cages equipped with a movement detector (infrared beam). The Y axis shows the number of beam interruptions over 10 hours; each bar represents a different experimental group. Nocturnal activity was recorded weekly between 4 and 5 weeks of age. Here, in contrast to in older animals (see FIG. 4B), MeCP2 KO mice did not yet exhibit less activity than wild type littermates, and treatment did not change activity levels. "N"=number of animals per group.

Figure 7:
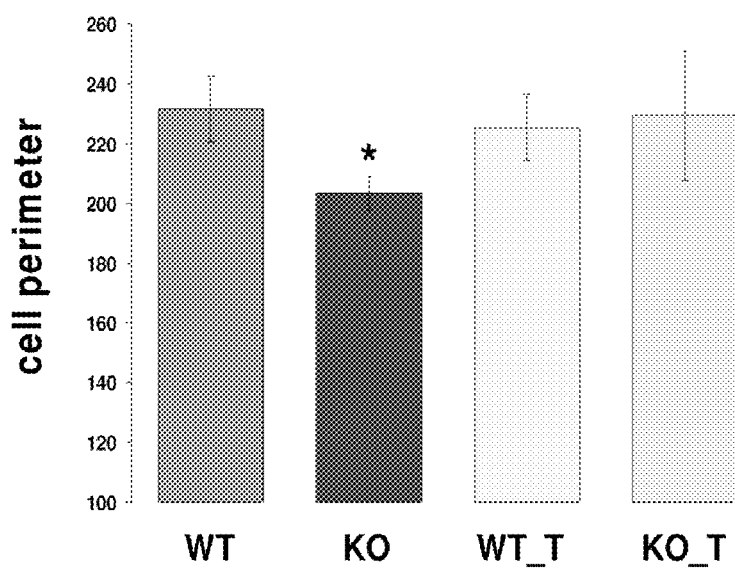

FIG. 7: (1-3)IGF-1 increases neuron soma size in the hippocampus.

Soma size (cell perimeter, μm) in neurons in the CA3 region of the hippocampus was significantly impaired in MeCP2 KO animals relative to Wild-type (WT). (1-3)IGF1 treatment increased average soma size in KO animals (KO_T). The treatment had no effect on soma size in wild type animals (WT_T).

Figure 8:
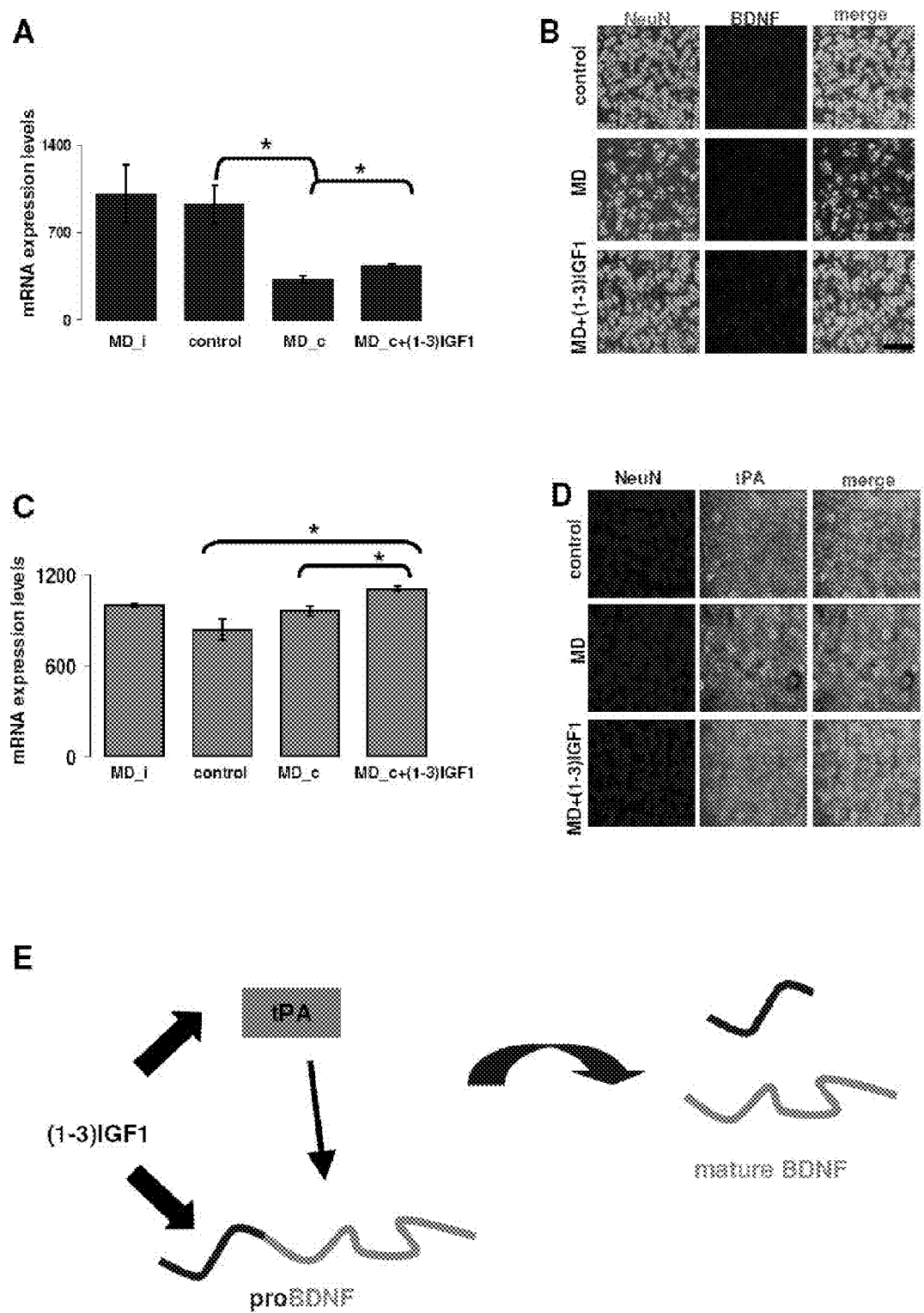

FIG. 8: (1-3)IGF-1 increases the expression and biological activity of BDNF and tPA.

A: Effects of (1-3)IGF-1 (GPE) treatment on the expression levels of BDNF at mRNA level. Monocular deprivation significantly decreases BDNF expression level in the contralateral V1. (1-3)IGF-1 treatment is able to increase expression though not to control levels. The RNA levels were obtained with the micro-array analysis described in Tropea et al., 2006.

B: Double staining for NeuN (green) and proBDNF (red) antibody. The protein expression confirms that (1-3)IGF-1 (GPE) treatment is able to modulate the effects of Monocular Deprivation by increasing BDNF protein expression, though not to control levels. Anti-pro BDNF and anti-NeuN were obtained from CHEMICON and used at a concentration of 1:500. The solutions and time of incubations are the following: preincubation in 5% BSA, 0.1% triton, 10% serum, PBS. Incubation with the primary antibodies was carried out at 4 degrees for 3 days in the following solution: 2% BSA, 5% serum, 0.1% triton, PBS. After washings in PBS secondary biotinylated (for pro-BDNF) or Alexa conjugated (for NeuN) antibodies (1:200) were incubated for 2 hours in the same solution of the primary antibodies. The pro-BDNF labeling was detected by adding extravidine tritc (Sigma—1:300).

C: Effects of (1-3)IGF-1 (GPE) treatment on the mRNA expression levels of tPA. GPE treatment significantly up-regulates tPA mRNA expression relative to both control and deprived animals.

D: Double staining for NeuN (red) and tPA (green) antibody. tPA staining, indicative of protein expression, is present in puncta in cell bodies and does not show prominent change in MD versus control. However, the expression level for tPA seems to be strongly increased by (1-3)IGF-1 (GPE) treatment. Anti-tPA was purchased from Oxford Biomedical Research and used at a concentration of 1:500. The conditions for incubation were the following: free floating sections were pre-incubated in blocking solution: 10% serum, 0.3% triton, PBS and then left overnight in the primary antibody mix: 1% serum, 0.3% triton, PBS, anti-tPA 1:500, anti Neu-N 1:500. The staining was visualized with secondary antibodies conjugated to Alexa488 and Alexa594.

E: Model of action of (1-3)IGF-1 (GPE) on BDNF activation: GPE promotes BDNF activity both by directly affecting its expression and by controlling its biological activation through tPA (which is known to cleave pro BDNF into mature BDNF).

Figure 9:
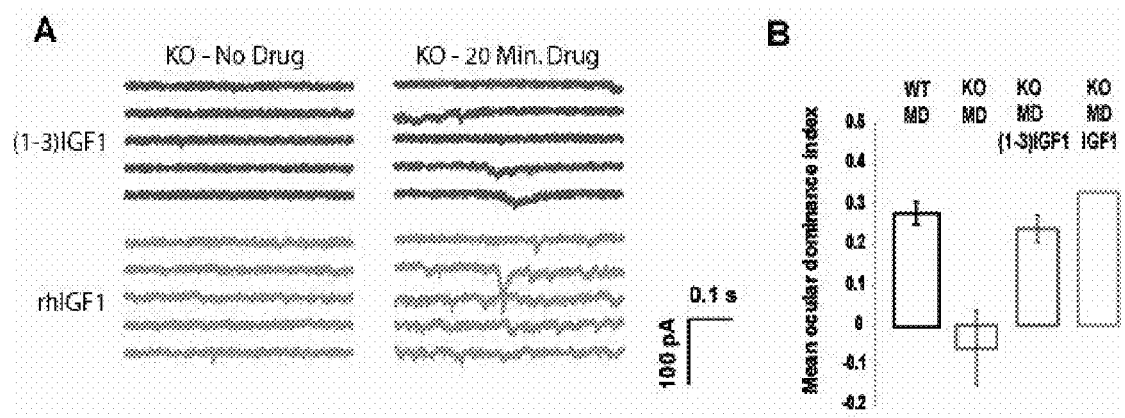

FIG. 9: Recombinant human IGF1 (rhIGF1) exhibits similar effectiveness as (1-3)IGF-1.

rhIGF1 produced a similar improvement as (1-3)IGF-1 in all maturational signatures measured, including (A) synaptic transmission levels, and (B) circuit stability (by preventing ocular dominance plasticity) in P60 MeCP2 KO mice.

It is to be understood that the drawings are illustrative only and are not required for enablement of the invention.

DETAILED DESCRIPTION OF THE INVENTION

Rett Syndrome (RTT) is a severe form of X-linked mental retardation caused by mutations in the gene coding for methyl CpG-binding protein 2 (MeCP2).

Reasonable evidence exists that synapses are in an immature state in MeCP2 knockout (KO) mice made as models of Rett Syndrome (RTT). A potential target of MeCP2 appears to be IGFBP3. IGFBP3 levels are upregulated in MeCP2 KO mice and in human RTT patients, and IGFBP3 transgenic mice have some of the brain pathology of MeCP2 KO mice.

Additionally, slowed brain growth and retardation of physical growth in RTT patients may indicate deficiencies in IGF1/growth hormone.

Low concentrations of IGF1 have been detected in the cerebrospinal fluid (CSF) of autistic patients (and patients with encephalopathies and white matter diseases); while no IGF1 deficit has been detected in the CSF of RTT patients, the sample sizes are small.

Here we show that adult Mecp2 mutant mice exhibit physiological signatures indicative of immature cortical circuitry, including weaker synaptic function in vitro and persistent cortical plasticity in vivo. Systemic treatment with (1-3)IGF-1, also referred to as GPE, a 3 amino acid active fragment of insulin-like growth factor 1 (IGF-1), restored the circuitry of the adult RTT mouse to more mature levels, by stimulating synaptic function and stabilizing the plasticity of the circuit. Additionally, treatment with the tri-peptide ameliorated bradycardia, improved locomotor function, and extended the life span of the knockout mice, which we observed to be significantly impaired in these areas. Our results suggest (1-3) IGF-1 as a strong candidate for pharmacological treatment of Rett Syndrome and potentially of other CNS disorders caused by delayed synapse maturation.

Based on these observations, we have determined that insulin-like growth factor (IGF1) or (1-3)IGF-1 (also referred to as glycyl-L-prolyl-L-glutamic acid, glycine-proline-glutamate, or GPE), a terminal fragment of IGF1, unexpectedly restore function in MeCP2 KO mice and, accordingly, are useful as human RTT therapeutics. Both of these molecules, and other analogous molecules such as (1-3)IGF-1 analogs that also can be used in the invention, cross the blood-brain barrier, and thus can be administered systemically as small molecule therapeutics for RTT and other disorders.

Without intending to be bound by any particular theory or mechanism of IGF1 action, it is believed that IGF1 may offset the effects of MeCP2 loss: by upregulating BDNF directly and through tPA cleavage of BDNF; by acting through PI3K to strengthen synapses or regulate a range of neuronal functions; by offsetting the effect of MeCP2 on IGFBPs; by upregulating inhibition and inhibitory circuits; or by directly influencing acetylation (e.g., of H3 and H4 histones) or MeCP2-mediated transcription.

Thus, the invention involves, in some aspects, administering an effective amount of IGF1, (1-3)IGF-1, a (1-3)IGF-1 analog, and/or a related therapeutic molecule to a subject to treat the subject. The term "treatment" or "treat" is intended to include prophylaxis, amelioration, prevention or cure of a condition. Treatment after a condition has stated aims to reduce, ameliorate or altogether eliminate the condition, and/or one or more of its associated symptoms, or prevent it from becoming worse. Treatment of subjects before a condition has started (i.e., prophylactic treatment) aims to reduce the risk of developing the condition and/or lessen its severity if the condition later develops. As used herein, the term "prevent" refers to the prophylactic treatment of subjects who are at risk of developing a condition which treatment results in a decrease in the probability that the subject will develop the condition, or results in an increase in the probability that the condition is less severe than it would have been absent the treatment. Treatments may reduce mortality, or extend life expectancy, of subjects having the condition as compared to subjects not treated as described herein in accordance with the invention.

A "subject" shall mean a human or animal including, but not limited to, a dog, cat, horse, cow, pig, sheep, goat, chicken, rodent, e.g., rats and mice, and primate, e.g., monkey. Preferred subjects are human subjects. The human subject may be a pediatric, adult or a geriatric subject.

The methods of the invention have broader application to disorders in addition to Rett Syndrome. Brain development, and hence developmental disorders of the brain, involve neurogenesis, neuronal migration, cellular differentiation and growth, and synaptic maturation. Because the data described herein pertain to the effects of IGF1/(1-3)IGF-1 on synaptic function and maturation and to the effect on molecules related to synaptic transmission and signaling, disorders, conditions or diseases that involve the synapse, including synaptic reorganization as a means to recover loss of function, are treatable in accordance with the invention. Thus, examples of disorders, conditions or diseases treatable by the methods and compositions of the invention include: Rett Syndrome, Autism and Autism Spectrum Disorders, Angelmann's Syndrome, tuberous sclerosis, Fragile X syndrome, schizophrenia, depression, neurodegenerative disorders including Parkinson's disease, Huntington's disease and Alzheimer's disease, stroke or brain trauma. In preferred embodiments, the disorders, conditions or diseases are those in which synaptic function and/or maturation is implicated as a causative factor in the disorder, condition or disease. In a particularly preferred embodiment, the disorder, condition or disease is Rett Syndrome.

The subject can be known to have a particular disorder, condition or disease that is amenable to such therapy, or may be suspected of having such a disorder, condition or disease. In some embodiments, the subject is free of symptoms otherwise calling for treatment with the IGF1, (1-3)IGF-1, (1-3) IGF-1 analog(s) and/or related therapeutic molecules.

Autism and Autism Spectrum Disorders are clinically diagnosed disorders with both single and complex multi-gene etiology. Single gene conditions such as Rett Syndrome and Fragile X contribute to a small fraction of autism cases directly (ca. 5-10%). However, because the single genes can also contribute to multi-gene conditions, therapeutics for single gene conditions have the potential to impact a much larger fraction of autism cases.

The applicability of the therapeutic methods of the invention to certain disorders, conditions or diseases is supported by an understanding of the IGF1 signaling pathway, including phosphoinositol-3 kinase (PI3K) and Akt/PKB.

PI3K is directly implicated in tuberous sclerosis, and in certain forms of autism that involve the PTEN gene. Recent evidence that BDNF acts through PI3K to effect changes in PSD95 and hence increase excitatory synaptic strength increases the potential importance of PI3K. Thus, increasing PI3K levels by IGF1, (1-3)IGF-1, (1-3)IGF-1 analog(s) and/or related therapeutic molecules may offset memory loss due to cognitive decline or due to neurodegenerative disorders including Parkinson's disease and Alzheimer's disease. Because changes in PSD95 are implicated in developmental disorders of synaptic dysfunction such as Fragile X syndrome, IGF1, (1-3)IGF-1, (1-3)IGF-1 analog(s) and/or related therapeutic molecules can be used for treating such disorders.

Akt is a central part of an anti-apoptotic pathway. It is implicated in countering loss of neurons due to stroke and Alzheimer's disease, and in neuro-protection after brain insult or injury. Akt affects the GSK3beta pathway, which is implicated in schizophrenia (lithium acts on this pathway). Application of IGF1 increases neurogenesis in the dentate gyrus of the hippocampus, by either the direct action of Akt or indirect actions of PI3K. Such neurogenesis is a major potential mechanism for anti-depressant action; hence IGF1, (1-3) IGF-1, (1-3)IGF-1 analog(s) and/or related therapeutic molecules can be used for treating schizophrenia or depression.

More broadly, IGF1 promotes neurogenesis and cell survival, neuronal growth and differentiation, and synaptic maturation. Thus, therapy with IGF1, (1-3)IGF-1, (1-3)IGF-1 analog(s) and/or related therapeutic molecules has the potential to be useful for a wide range of neurodegenerative disorders of diverse etiology, including Parkinson's disease, Huntington's disease and Alzheimer's disease, multiple sclerosis and spinal cord diseases such as ALS.

In certain cases, the disorders can be treated with combination therapy. (1-3)IGF-1/IGF1 consolidates synapses and promotes certain kinds of plasticity (which rely on stabilizing a few weak synapses out of a broad set potentially available). The latter is important for promoting functional reorganization after stroke, particularly in combination therapy, such as (in addition to IGF1, (1-3)IGF-1, (1-3)IGF-1 analog(s) and/or related therapeutic molecules) rehabilitation therapy and administration of other molecules such as tPA, BDNF, a molecule that regulates inhibition such as a benzodiazepine, or a molecule that is a neurotransmitter agonist, antagonist or analog. Such molecules provide synergistically beneficial effects for treatment.

Many benzodiazepines are well known in the art, including hypnotic benzodiazepines and anxiolytic benzodiazepines. Similarly, a related class of drugs that interact with benzodiazepine receptors, the "nonbenzodiazepines", also can be used in the same manner as benzodiazepines in the methods described herein.

In a particular embodiment, as shown in the Examples below, (1-3)IGF-1 upregulates tPA. tPA promotes functional and structural reorganization at synapses. Thus (1-3)IGF-1 and tPA work in positive feedback. Similarly, (1-3)IGF-1 upregulates BDNF, and IGF1, (1-3)IGF-1, (1-3)IGF-1 analog(s) and/or related therapeutic molecules and BDNF are highly likely to work better in combination than individually.

The invention involves in certain embodiments methods of treatment comprising administering an effective amount of a (1-3)IGF-1 analog. As used herein, a "(1-3)IGF-1 analog" (or a "GPE analog") includes compounds that have pharmacological properties and therapeutic activities substantially similar to those of (1-3)IGF-1.

(1-3)IGF-1 analogs known in the art can be used in the invention. EP 0 366 638 describes the (1-3)IGF-1 analogs Gly-Pro and Pro-Glu. WO02/16408 describes a variety of (1-3)IGF-1 analogs including those containing substitutions where the Gly of Gly-Pro-Glu is replaced by any of Ala, Ser, Thr, or Pro; where the Pro of Gly-Pro-Glu is replaced by any of Ala, Ser, Thr, or Gly; and where the Glu of Gly-Pro-Glu is replaced by any of Asn, Asp, or Gln. Additional (1-3)IGF-1 analogs described in WO02/16408 include (1-3)IGF-1 amides and stearates. Specific analogs described in WO02/16408 also include the following: (1-3)IGF-1 amide, (1-3)IGF-1 stearate, Gly-Pro-D-glutamate (GP-D-E) Gly-Pro-Thr (GPT) Gly-Glu-Pro (GEP) Glu-Gly-Pro (EGP) Glu-Pro-Gly (EPG), all of which can be readily synthesized using standard techniques. U.S. Pat. No. 7,041,314 describes additional (1-3)IGF-1 analogs and peptidomimetics that are useful in accordance with the invention.

The (1-3)IGF-1 analog also can be a peptide as described herein that is non-hydrolyzable, e.g., having one or more (i.e., one or two) non-hydrolyzable peptide bonds or amino acids. Preferred non-hydrolyzable peptides include peptides comprising D-amino acids, peptides comprising a -psi[CH$_2$NH]-reduced amide peptide bond, peptides comprising a -psi [COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

Additional (1-3)IGF-1 analogs that can be used in accordance with the present invention can be identified as having one or more properties that are at least substantially equivalent to (1-3)IGF-1, such as the properties described herein, or properties of (1-3)IGF-1 that can be assessed by various assays known to those of skill in the art, such as assays of the ability to cross the blood brain barrier, etc.

Other "related therapeutic molecules" that can be used in a similar manner as IGF1, (1-3)IGF-1, (1-3)IGF-1 analog(s) to treat the disorders as described herein include IGF-1 secretagogues, growth hormones or precursors, growth hormone secretagogues, growth hormone releasing peptides, growth hormone releasing hormone and its analogs.

IGF-1 secretagogues are known in the art, for example as described in United States published patent application 2006/0100287.

Growth hormones or precursors thereof include human growth hormone (hGH) such as Nutropin (Genentech), Protropin (Genentech), Humatrope (Lilly), Genotropin (Pfizer), Norditropin (Novo), Saizen (Merck Serono) and Omnitrope (Sandoz).

Growth hormone secretagogues, growth hormone releasing peptides, growth hormone releasing hormone and analogs include ipamorelin and derivatives thereof (e.g., growth hormone secretagogues, derived from ipamorelin, are described in Ankersen et al. Eur. J. Med. Chem. 34 (10): 783-790, 1999), MK677 (Merck; N-[1(R){[1,2-dihydro-1-methanesulfonyl-spiro-(3H-indole-3,4'-piperidine)-1'-yl]carbonyl}-2-(phenylmethoxy)-ethyl]-2-amino-2-methylpropanamide methanesulfonate), NN703 (tabimorelin, Novo Nordisk) and derivatives thereof (GH secretagogues based on modifications in the C-terminal end of NN703 are described in Ankersen et al. Eur. J. Med. Chem. 35 (5): 487-497, 2000), SM 130686 (Sumitomo) capromorelin (Pfizer), sermorelin (Salk Institute, Bio-Technology General), ghrelin, hexarelin (examorelin), tabimorelin; CP 464709 (Pfizer), LY 426410 (Lilly), LY 444711 (Lilly; shown to increase IGF1 levels (Seyler et al., Drug Devel. Res. 49 (4): 260-265, 2000)), 8-(aminoalkoxyimino)-8H-dibenzo[a,e]triazolo[4,5-cyclo-heptenes as disclosed in WO2002057241, 2-substituted dibenzo[a,e]1,2,3-triazolo[4,5-c][7]annulen-8-ones as described in WO2002056873, growth hormone releasing peptides GHRP-1, GHRP-2 and GHRP-6 as described in U.S. Pat. No. 4,411,890, and publications WO 89/07110, WO 89/07111, B-HT920, growth hormone releasing hormone (GHRH, also designated GRF) and its analogs, and additional growth hormone secretagogues as described in U.S. Pat. No. 6,559,150.

IGF1, (1-3)IGF-1, (1-3)IGF-1 analog(s) and/or related therapeutic molecules are administered in an amount effective to treat the disorder, condition or disease in the subject. An effective amount is a dosage of the therapeutic agent(s) sufficient to provide a medically desirable response. For example the desirable response may be inhibiting the progression of the disorder, condition or disease. This may involve only slowing the progression of the disorder, condition or disease temporarily, although more preferably, it involves halting the progression of the disorder, condition or disease permanently. This can be monitored by routine diagnostic methods known to those of ordinary skill in the art.

It should be understood that the therapeutic agents of the invention are used to treat or prevent the disorder, condition or disease, that is, they may be used prophylactically in subjects at risk of developing the disorder, condition or disease. Thus, an effective amount is that amount which can lower the risk of, lessen the severity of, or perhaps prevent altogether the development of the disorder, condition or disease.

The factors involved in determining an effective amount are well known to those of ordinary skill in the art and can be addressed with no more than routine experimentation. It is generally preferred that a maximum dose of the therapeutic agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

IGF1, (1-3)IGF-1, (1-3)IGF-1 analog(s) and/or related therapeutic molecules may be administered alone, in a pharmaceutical composition or combined with other therapeutic agent(s) or regimens. Optionally other therapeutic agent(s) may be administered simultaneously or sequentially. When the other therapeutic agent(s) are administered simultaneously they can be administered in the same or separate formulations, but are administered at the same time. The other therapeutic agent(s) may be administered sequentially with one another and with the IGF1, (1-3)IGF-1, (1-3)IGF-1 analog(s) and/or related therapeutic molecules when the administration of the other therapeutic agent(s) and the IGF1, (1-3)IGF-1, (1-3)IGF-1 analog(s) and/or related therapeutic molecules are temporally separated. The separation in time between the administration of these compounds may be a matter of minutes or it may be longer, such as 1, 2, 3, 4, 5, 6, 7, 8, 9, 10, 11 or 12 hours, or more, including 1, 2, 3, 4, 5, 6, 7 days or more.

The pharmaceutical compositions used in the methods of the invention are preferably sterile and contain effective amounts of the IGF1, (1-3)IGF-1, (1-3)IGF-1 analog(s) and/or related therapeutic molecules for producing the desired response in a unit of weight or volume suitable for administration to a subject. The doses of pharmacological agent(s) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Several studies have been conducted in which (1-3)IGF-1 or IGF1 was administered systemically and produced an effect on brain function.

In Tropea et al. (*Nat Neurosci* 9, 660-8, 2006), (1-3)IGF-1 was infused IP, simultaneously to monocular deprivation (MD). (1-3)IGF-1 was injected at about 20 μg/gr/day for 7 days.

In another study (Sizonenko et al., *Brain Res* 922, 42-50, 2001) performed on developing (P21) rats there was one single injection of (1-3)IGF-1 (6.7 μg/gr) after 2 hours of induced ischemia.

In another study (Lupien et al., *J Neurosci Res* 74, 512-23, 2003), diabetic rats were treated with IGF1 in order to improve the learning deficits normally observed in diabetes. Adult rats (about 400 gr) were implanted with minipumps that released 20 μg/day per animal, which is equivalent to about 0.05 μg/gr per day. In this case the release was subcutaneous for 7.5 weeks.

In another study (Saatman et al., *Exp Neurol* 147, 418-27, 1997) observing the improvement in motor learning, IGF1 was delivered for 14 days, either by subcutaneous injections each 12 hours 1 μg/gr (equivalent to 2 μg/gr per day), or by a subcutaneous pump (4 μg/gr/day) in monkeys.

Aberg et al. (*J Neurosci* 20, 2896-903, 2000) delivered recombinant IGF1 (Genentech, South San Francisco, Calif.) to P50 rats subcutaneously with a minipump for six days or 20 days, using a dosage of 1.25 mg/kg/day and 0.9 mg/kg/day, respectively.

The FDA approved dose for Increlex (Tercica, rhIGF1) is 0.08-0.12 mg/kg/BID, which equals 0.16-0.24 mg/kg/day.

For the methods of the invention described herein, preferred doses of IGF1 are about 0.01-50 mg/kg/day, more preferably about 0.1-10 mg/kg/day, administered in one dose or in multiple daily doses. IGF1 preferably is human IGF1 (hIGF1), and preferably is recombinantly produced (rIGF1), most preferably recombinant human IGF1 (rhIGF1). More preferably, the doses of recombinant IGF1 are about 0.1-2 mg/kg/day. The FDA approved dose for rhIGF1 is particularly contemplated for use in the methods of the invention, although as described elsewhere herein, higher or lower doses also are contemplated.

For the methods of the invention described herein, preferred doses of (1-3)IGF-1 are about 0.1-100 mg/kg/day, administered in one dose or in multiple daily doses. More preferably, the doses of (1-3)IGF-1 are about 6-20 mg/kg/day.

Various modes of administration are known to those of ordinary skill in the art which effectively deliver the pharmacological agents of the invention to a desired tissue, cell, or bodily fluid. Administration of the molecules of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a mode of administration.

The invention is not limited by the particular modes of administration disclosed herein. Standard references in the art (e.g., *Remington's Pharmaceutical Sciences*, 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g., for testing purposes or veterinary therapeutic purposes, is carried out under substantially the same conditions as described above. It will be understood by one of ordinary skill in the art that this invention is applicable to both human and animal diseases.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the compounds may be in powder form for constitution with a suitable vehicle (e.g., saline, buffer, or sterile pyrogen-free water) before use.

Compositions suitable for oral administration may be presented as discrete units, such as capsules, tablets, pills, lozenges, each containing a predetermined amount of the active compound(s). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, sorbitol or cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the molecule(s) or by release of the biologically active molecule(s) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

One may dilute or increase the volume of the therapeutic agent with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For administration intranasally or by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the molecule(s). The molecule(s) are delivered to the lungs of a mammal while inhaling and traverse across the lung epithelial lining to the blood stream.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The molecule(s) are suitable for use in a variety of drug delivery systems. For a brief review of methods for drug delivery, see Langer, *Science* 249:1527-1533, 1990, which is incorporated herein by reference.

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The invention also contemplates the use of kits. In some aspects of the invention, the kit can include a pharmaceutical preparation vial, a pharmaceutical preparation diluent vial, and the molecule(s) of the invention as described herein. The vial containing the diluent for the pharmaceutical preparation is optional. The diluent vial contains a diluent such as physiological saline for diluting what could be a concentrated solution or lyophilized powder of the molecule(s). The instructions can include instructions for mixing a particular amount of the diluent with a particular amount of the concentrated pharmaceutical preparation, whereby a final formulation for injection or infusion is prepared. The instructions may include instructions for treating a subject with an effective amount of the molecule(s). It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

Also contemplated is the use of diagnostic methods in combination with therapy. For example, given that Rett Syndrome is known to be associated with and caused by mutations or variations in the gene encoding MeCP2 in a large majority of cases, a subject can be first screened for such mutations. This can be done to determine the suitability of the subject for treatment with IGF1, (1-3)IGF-1, (1-3)IGF-1 analog(s) and/or related therapeutic molecules as described herein. Subjects having other diseases, conditions and disorders that have a genetic basis and are amenable to the therapies described herein also can diagnosed and treated in the same way. In particular, subjects with mutations or variations in genes that are targets of MeCP2 or are downstream of MeCP2 are amenable to the therapies described herein and can be diagnosed and treated in the same way.

Standard clinical diagnostic methods are well known in the art. Typically these methods include obtaining a sample from the subject, which may be without limitation a tissue sample, biopsy, fluid sample (e.g., blood, urine, saliva, cerebrospinal fluid), etc., and then subjecting the sample to the diagnostic procedure. Many well-known methodologies are available to the practitioner to analyze the sample, such as various nucleic acid detection and amplification methods, including polymerase chain reaction-based methods, and various protein detection methods, including antibody-based detection methods. In other instances it may be possible to use imaging techniques for non-invasive diagnosis.

Diagnostic methods also may be combined with therapeutic methods to follow the course of disease during therapy, and to aid in the selection of appropriate therapy. Such applications of diagnostic methods in combination with therapeutic methods is routinely practiced in the medical arts.

The present invention is further illustrated by the following Examples, which in no way should be construed as further limiting.

EXAMPLES

Example 1

Rett Syndrome (RTT) is an X-linked neurological disorder that affects 1 in 10,000-15,000 live births (Chahrour and Zoghbi, 2007). The disorder is characterized by seemingly normal postnatal development followed by a sudden growth deceleration associated with progressive loss of acquired motor and language skills, stereotypic hand movements, muscle hypotonia, autonomic dysfunctions and severe cognitive impairment. There remains no specific treatment for RTT and management is mainly symptomatic and individualized.

In ~85% of patients suffering from RTT, the cause is a mutation in the gene coding for methyl CpG-binding protein 2 (MECP2) (Amir et al., 1999), a global transcriptional repressor (Nan et al., 1998) that is strongly expressed in the central nervous system (CNS) following the onset of neuronal maturation and synaptogenesis (Cohen et al., 2003; Shahbazian et al., 2002b). Mouse models have been generated in which CNS-specific deletion of Mecp2 is sufficient to cause Rett-like symptoms (Gemelli et al., 2006; Guy et al., 2001; Shahbazian et al., 2002a), and activation of the MeCP2 protein even at late stages of the disease can rescue the mutant phenotype (Giacometti et al., 2007; Guy et al., 2001). An important feature of RTT suggested by mouse models is therefore also that it is reversible—the CNS circuits involved apparently do not atrophy but rather remain in a labile, immature state, whereby subsequent activation of the circuits can repair the syndrome's consequences. Cortical and hippocampal brain circuits in MeCP2 mutant mice, for example, are characterized by weaker excitatory synapses (Chao et al., 2007; Dani et al., 2005; Nelson et al., 2006) that resemble those of a normal immature circuit.

While Mecp2 target genes that might contribute to this phenotype have been difficult to identify (Tudor et al., 2002) the best characterized target of MeCP2 regulation is the brain derived neurotrophic factor BDNF (Chen et al., 2003), which is generally known to trigger maturation and promote stronger synapses (Schuman, 1999), and can indeed restore activity levels in the mutant mice and relieve some symptoms of the mutant phenotype (Chang et al., 2006). Unfortunately, the therapeutic utility of BDNF is hampered by its poor efficiency at crossing the blood brain barrier. Nevertheless, a therapeutic intervention in humans might thus arise from identifying an agent similarly capable of stimulating synaptic maturation.

A second pleiotrophic growth factor with similar promise in CNS therapy is insulin-like growth factor 1 (IGF-1). Like BDNF, IGF1 is widely expressed in the CNS during normal development (Bondy, 1991), strongly promotes neuronal cell survival and synaptic maturation (Liu et al., 1993), and facilitates the maturation of functional plasticity in the developing cortex (Tropea et al., 2006). While BDNF stimulates synaptic strengthening via a pathway involving PI3K/pAkt/PSD95 (Yoshii and Constantine-Paton, 2007) to bolster the postsynaptic apparatus and contribute to synaptic function, IGF1 stimulates the same pathway as well (Tropea et al., 2006; Zheng and Quirion, 2004), and has been shown to elevate excitatory postsynaptic currents significantly (Ramsey et al., 2005; Xing et al., 2007). The biological action of IGF1 is also regulated by the binding of IGF binding proteins (IGFBP 1-6) which may be of significance to RTT and other disorders. IGFBP3, for example, has a binding site for the MeCP2 protein, and since MeCP2 null mice and Rett patients lack this methylation repressor, they express aberrantly high levels of IGFBP3 (Itoh et al., 2007) which in turn inhibits IGF1-depressed IGF1 levels have indeed been observed across several forms of ASD (Riikonen et al., 2006).

Unlike BDNF, IGF1 is capable of crossing the blood-brain barrier, particularly in its tri-peptide form (1-3)IGF-1 (Baker et al., 2005), where it retains strong neurotrophic efficacy (Guan et al., 2004; Itoh et al., 2007; Saura et al., 1999; Sizonenko et al., 2001). Given this versatility, and the fact that IGF1 has already been approved for human clinical trials (citation needed), IGF-1 signaling offers a comparable target to BDNF for engaging key molecular pathways to stimulate synaptic maturation and reverse the RTT phenotype, but in a format that is more amenable to therapeutic administration to RTT patients. We therefore investigated the potential of (1-3) IGF-1, delivered systemically, to overcome the synaptic and neuronal immaturities that are characteristic of RTT physiopathology (Johnston et al., 2001; Kaufmann et al., 1997), and ameliorate Rett-like symptoms in a mouse model of the disease.

Experimental Procedures

Mice mating and genotyping: we used the MeCP2 germline null allele from Chen et al. (Chen et al., 2001). Genotyping was performed as in Chen et al. (Chen et al., 2001).

(1-3)IGF-1 treatment: For the survival measurements, the nocturnal activity analysis and the immunoblot analysis, (1-3) IGF-1 (Bachem Biosciences # H22468) was administered daily via intra-peritoneal injections (0.01 mg/g body weight, vehicle=saline, 0.01% BSA). The treatment was started at P15 and maintained throughout the course of the experiments. For intracellular physiology experiments, the mice were injected daily (0.01 mg/g body weight, vehicle=saline, 0.01% BSA) for 2 weeks, from P15 to P28-P32 when they were used for acute slice preparation. For optical imaging experiments, mice were injected with (1-3) IGF-1 (0.02 mg/g body weight, vehicle=saline, 0.01% BSA) daily from the day of the lid suture to the day of imaging.

Slice physiology preparation: Coronal sections (300 μm thick) at or near sensorimotor cortex were cut in <4° C. ACSF using a Vibratome. Slices were incubated at 37° C. for 20 minutes after slicing, and at room temperature for the remainder of the experiment. Slices were transferred to a Warner chamber and recordings were taken from visually identified pyramidal neurons located in layer 5. Artificial cerebral spinal fluid (ACSF) contained 126 mM NaCl, 25 mM NaHCO3, 1 mM NaHPO4, 3 mM KCl, 2 mM MgSO4, 2 mM CaCl2, and 14 mM dextrose, was adjusted to 315-320 mOsm and 7.4 pH, and was bubbled with 95% O2/5% CO2. The intracellular pipette solution contained 100 mM potassium gluconate, 20 mM KCl, 10 mM HEPES, 4 mM MgATP, 0.3 mM NaGTP, and 10 mM Na-phosphocreatine.

Intracellular whole-cell recordings: Borosilicate pipettes (3-5 MΩ, WPI) were pulled using a Sutter P-80 puller (Sutter Instruments). Cells were visualized with an Achroplan 40× water-immersion lens with infrared-DIC optics (Zeiss) and detected with an infrared camera (Hamamatsu) projecting to a video monitor. Experiments were driven by custom acquisition and real-time analysis software written in Matlab (Mathworks, Natick, Mass.) using a Multiclamp 700B amplifier (Axon Instruments) connected to a BNC-2110 connector block and M-Series dual-channel acquisition card (National Instruments). Gigaseal and rupture was achieved and whole-cell recordings were continuously verified for low levels of leak and series resistance. For each recording, a 5 mV test pulse was applied in voltage clamp ~10 times to measure input and series resistance. Then in current clamp ~10 pulses (500 ms, 40-140 pA at 10 pA increments), were applied to quantify evoked firing rates and cellular excitability. Access resistance, leak, and cellular intrinsic excitability were verified to be consistent across groups. Finally, spontaneous EPSCs under voltage clamp at −60 mV were sampled at 10 kHz and low-pass filtered at 1 kHz. Analysis was performed using a custom software package written in Matlab, with all events detected according to automated thresholds and blindly verified for each event individually by the experimenter.

Golgi staining: Samples (<1 cm) from P28 mice were fixed in 10% formalin and 3% potassium bichromate for 24 hours. Tissue was then transferred into 2% silver nitrate for 2 days in the dark at room temperature. Sections from these samples were then cut at 50 μm thickness into distilled water. Sections corresponding to motor cortex were mounted onto slides, air dried for 10 minutes, and then dehydrated through sequential rinses of 95% alcohol, 100% alcohol, and xylene, and then sealed with a coverslip. Images were acquired at 10× (whole cell) and 100× (spine imaging) using a Zeiss Pascal 5 Exciter confocal microscope.

Optical imaging of intrinsic signals: Adult (>P60) wild type (SVEV or BL6) and MeCP2 (+/−) mutant females (BL6) were used for this experiment. The wild type control group was composed of both wild type littermates of MeCP2+/− females or wild type age matched SVEV females. For monocular deprivation, animals were anesthetized with Avertin (0.016 ml/g) and the eyelids of one eye was sutured for 4 days. Prior to imaging, the suture was removed and the deprived eye re-opened. Only animals in which the deprivation sutures were intact and the condition of the deprived eye appeared healthy were used for the imaging session. For IGF-1 signaling activation, a solution containing (1-3) IGF-1 was injected intra-peritoneally (IP) daily for the entire period of deprivation. For the imaging sessions mice were anesthetized with urethane (1.5 g/kg; 20% of the full dosage was administered IP each 20-30 minutes up to the final dosage, 0.02 ml of cloroprothixene 1% was also injected together with the first administration). The skull was exposed and a custom-made plate was glued on the head to minimize movement. The skull was thinned over V1 with a dremel drill and covered with an agarose solution in saline (1.5%) and a glass coverslip. During the imaging session, the animal was constantly oxygenated, its temperature maintained with a heating blanket and the eyes periodically treated with silicone oil; physiological conditions were constantly monitored. The anesthetized mouse was placed in front of a monitor displaying a periodic stimulus presented to either eye, monocularly; the stimulus consisted of a drifting vertical or horizontal white bar of dimensions 9°×72°, drifting at 9 sec/cycle, over a uniformly gray background. The skull surface was illuminated with a red light (630 nm) and the change of luminance was captured by a CCD camera (Cascade 512B, Roper Scientific) at the rate of 15 frames/sec during each stimulus session of 25 minutes. A temporal high pass filter (135 frames) was employed to remove the slow signal noise, after which the signal was computer processed in order to extract, at each pixel, the temporal Fast Fourier Transform (FFT) component corresponding to the stimulus frequency. The FFT amplitude was used to measure the strength of the visual evoked response to each eye. The ocular dominance index was derived from each eye's response (R) at each pixel as ODI=(Rcontra−Ripsi)/(Rcontra+Ripsi). The binocular zone was defined as the region activated by the stimulation of the eye ipsilateral to the imaged hemisphere.

Heart rate measurements: Real time cardiac pulse rate was measured using a tail clip sensor (Mouse OX Oximeter—Oakmont, Pa.). Mice were not anesthetized but physically restrained in a fitted open plastic tube. Prior to the recording session the tube was placed overnight in the cages housing the experimental animals to allow habituation. Body temperature was maintained at ~82-84° F. throughout the recording time. We recorded 3 trials of 15 minutes for each mouse, mice were 8 weeks old and treated with vehicle or (1-3)IGF-1 from P15.

Nocturnal activity measurements: Spontaneous motor activity was measured by using an infrared beam-activated movement-monitoring chamber (Opto-Varimax-MiniA; Columbus Instruments, Columbus, Ohio). For each experiment, a mouse was placed in the chamber at least 3 h before recordings started. Movement was monitored during the normal 12-h dark cycle (7 p.m. to 7 a.m.). One dark cycle per animal per time point was collected.

Results

To test whether (1-3)IGF1 treatment would impact the development of cardinal features of the RTT disease, 2 week old mutant animals were given daily intra-peritoneal injections for the course of their lifespan. Measurements of synaptic physiology, synaptic molecular composition, and cortical plasticity were then acquired as detailed below, along with health-related measurements such as heart rate, locomotor activity levels, and lifespan.

Effects of (1-3)IGF-1 on the Synaptic Physiology of MeCP2 Mutant Mice.

Figure 1:
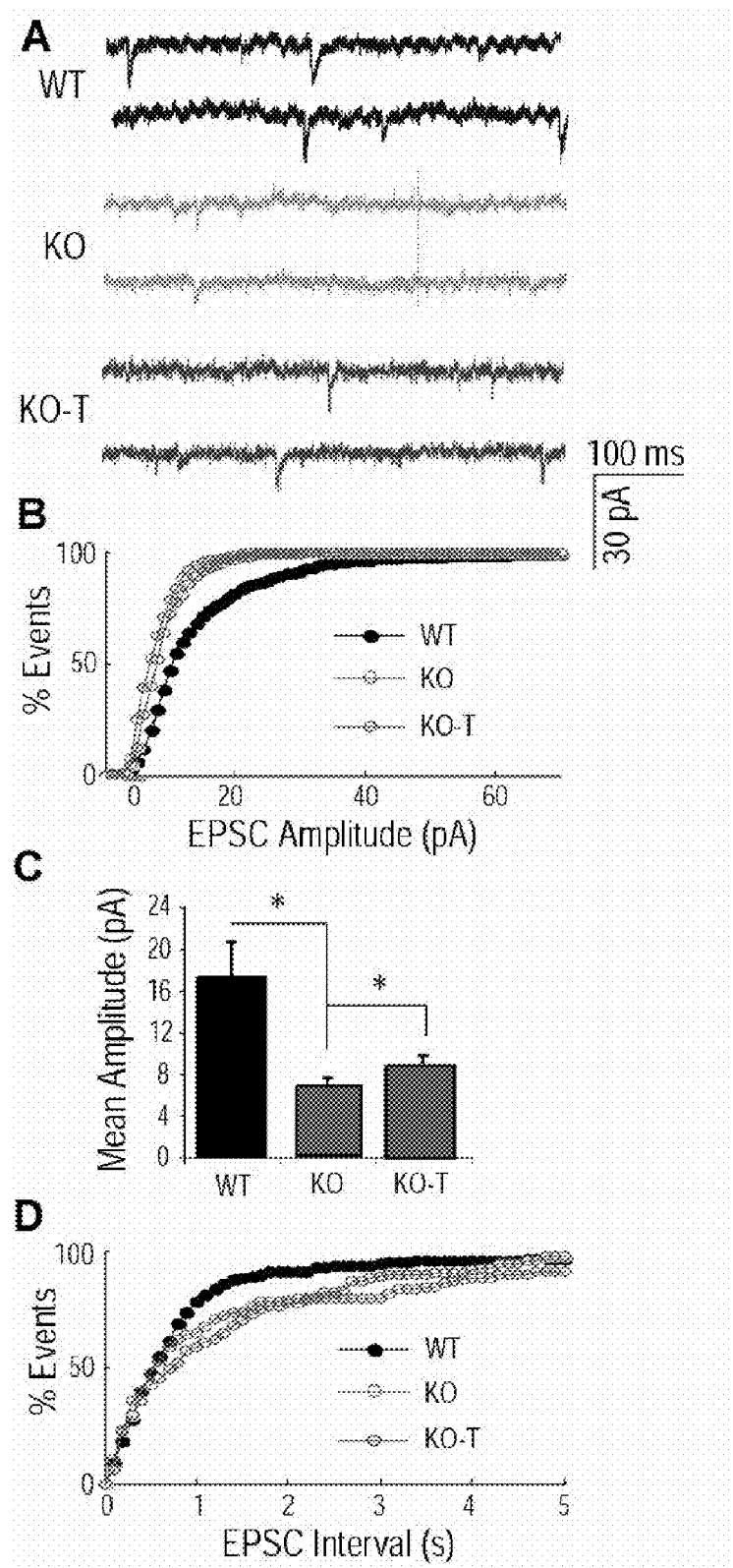
FIG. 1: Increased amplitude of synaptic currents for layer 5 pyramidal neurons in (1-3)IGF-1 treated MeCP2 KO animals.
A. Representative traces from intracellular recordings of spontaneous excitatory postsynaptic currents (EPSCs) in acute cortical slices. Traces are presented for wild type (WT), knockout (KO), or KO treated with (1-3)IGF-1 for two weeks (KO-T). Mice were 28-32 days old.
B. Cumulative distributions of EPSC amplitudes, across all cells measured. Distributions indicate an increased percentage of events with smaller amplitudes in KO vs. WT. (1-3)IGF-1 treatment partially but significantly reversed this trend.
C. Mean EPSC amplitude for EPSCs observed per neuron, across all cells recorded for WT, KO and KO-T. Mean EPSC amplitude was significantly reduced in KO neurons compared to WT ones. Mean EPSC amplitude was modestly but significantly increased in KO-T compared to KO ones.

Recent studies have reported that neurons across multiple brain regions of MeCP2−/y mice display a profound reduction in spontaneous activity (Chang et al., 2006; Chao et al., 2007; Dani et al., 2005; Nelson et al., 2006) a phenotype that was rescued by overexpression of BDNF (Chang et al., 2006). Similarly, acute application of an IGF1 derivative has been shown to elevate evoked excitatory postsynaptic current (EPSC) amplitudes by 40% in rat hippocampal cultures (Ramsey et al., 2005; Xing et al., 2007). To thus test the efficacy of (1-3)IGF1 in rescuing the MeCP2−/y physiological phenotype, we acquired intracellular whole cell recordings in acute brain slices, measuring excitatory synaptic drive (spontaneous EPSC amplitude and frequency) in layer 5 cortical neurons (FIG. 1A). Here, EPSCs recorded from −/y animals were significantly reduced in amplitude compared to EPSCs measured in wild-type animals (FIG. 1B). The trend was partially reversed in EPSCs recorded from MeCP2−/y animals treated with (1-3)IGF-1, which were significantly larger in amplitude than EPSCs from MeCP2−/y mice treated with vehicle (FIG. 1B). These differences were also seen when averaging across cells (FIG. 1C). Throughout these measurements, access resistance, leak, and cellular intrinsic excitability were also verified to be consistent across groups (data not shown). Quantifying EPSC intervals also showed a slight increase in the interval between EPSC events (reduced EPSC frequency) between wild-type and MeCP2−/y animals (P=0.04, Kolmogorov-Smirnov test; FIG. 1D). Our findings thus indicate that the reduction of excitatory synaptic drive in cortical cells of MeCP2−/y mice, and its partial rescue following (1-3)IGF-1 treatment, are due in part to a change in EPSC amplitude as a consequence of a change in the strength of the synapses mediating excitatory transmission in this region.

(1-3)IGF-1 Treatment Stimulates Cortical Spine Maturation

We hypothesized that RTT arises from a defect in synaptic maturation and stabilization, which should be physically evident in the structure of dendritic contacts. Also, given that the knockout was characterized by deficits in excitatory synaptic transmission that were partially ameliorated by treatment with (1-3)IGF1, we expected there to be potentially be comparable changes in the structure and density of dendritic spines. We thus used golgi staining to label neurons sparsely and distinctly, and applied high-resolution confocal imaging to measure dendritic spine density and morphology in the labeled cells, restricting analysis to layer 5 pyramidal neurons in sections of motor cortex from critical period mice (P28).

While low-magnification imaging clearly delineated the extent of the dendrites of these pyramidal cells (FIG. 2A) we could use higher magnifications to count synaptic contacts (FIG. 2B) and determine the morphological class of each spine. We classified spines as either large and bulbous ("mushroom", M), short and stubby ("stubby", S), short and thin ("thin", T) or filopodia (F). Comparing the density of spines per unit branch revealed a trend of decreased spine density in knockout neurons that was largely ameliorated in the knockout with treatment (FIG. 2C). Analyzing the proportion of each spine type that was present in each condition (FIG. 2D) indicated a deficit in mushroom-type (mature) spines in the knockout that was partially rescued with treatment, and an over-representation of thin-type (immature) spines in the knockout that was not impacted by the treatment.

Finally, quantification of branch thickness (FIG. 2E) did not detect any difference between the conditions.

Together these results suggest the potential for deficits in the number and maturational status of dendritic contacts in the knockout to underpin functional defects in excitatory transmission, in a manner that can be partially rescued following treatment with (1-3)IGF1.

MeCP2 Deficiency Causes Aberrant Ocular Dominance Plasticity in Adult Mice

The functional data (FIG. 1) and structural data (FIG. 2) presented thus far, together with the timing of MeCP2 expression (Shahbazian et al., 2002b) and data from rescue experiments (Giacometti et al., 2007; Guy et al., 2007) suggest that MeCP2 deficiency might cause incomplete synaptic and neuronal maturation (Johnston et al., 2001; Kaufmann et al., 1997). If the symptoms of Rett arise from an immaturity of brain circuitry that leaves synapses in an under-developed or regressed state, we hypothesized that an additional outcome would be that cortical circuitry in MeCP2 KO mice would be unable to sustain stable representations, and synapses will be more labile and prone to change in response to their environment. We assessed this using a well-established model for testing cortical plasticity known as "ocular dominance plasticity" (Hofer et al., 2006), in which the visual cortex response to each of two eyes is measured (FIG. 5A), the more dominant eye is then closed for a few days (monocular deprivation, MD), after which the cortical response is measured again to see how even a few days of modified input can change the responses to the two eyes. In mice, the contralateral eye normally dominates in cortex (FIGS. 5A and 5C), but closing the dominant eye can lead to cortical "takeover" by the other eye if the circuit is still immature and labile (Gordon and Stryker, 1996), thus leading to a shift in the "ocular dominance index" (ODI) (FIGS. 5B and 5D). If the brain circuitry is mature and stable however, as in adult animals, there will not be a change in ODI (FIG. 5E).

We reasoned that if synaptic development was arrested in MeCP2-deficient mice, synapses in visual cortex of adult mice would still be sensitive to brief MD. To measure cortical responses elicited by stimulation of the eyes, we used optical imaging of intrinsic signals, a technique which detects level of deoxygenated hemoglobin, is related closely to neuronal activity, and is a highly sensitive and reliable measure of cortical plasticity (Hofer et al., 2006; Smith and Trachtenberg, 2007). Because adult MeCP2−/y mice do not tolerate the anesthetic required for this analysis, we used MeCP2 heterozygous females which develop milder symptoms (FIG. 3). We first measured ocular dominance plasticity in young WT mice (postnatal day 28) and found that 4 day MD induced a robust shift in the population ODI (FIG. 3A). However, repeating this paradigm in WT adult mice (P60) failed to produce a shift in the population ODI (FIG. 3B) when comparing non-deprived mice (solid black traces) to monocularly-deprived counterparts (dashed black traces). In contrast, age-matched MeCP2 mutants (+/−) showed a significant shift in the visually driven response in favour of the open eye (FIG. 3B, pink traces). These results reveal the persistence of rapid synaptic plasticity following unbalanced visual drive in the adult MeCP2 mutant visual cortex, a feature that is typical of an immature cortex and is consistent with a deficit in synaptic maturation or stabilization following MeCP2 deficiency.

Ocular Dominance Plasticity in Adult MeCP2+/− Mice is Prevented by (1-3)IGF-1 Treatment Developmental changes in OD plasticity are controlled in part by the activation of the IGF-1 pathway, and administration of (1-3)IGF-1 can abolish OD plasticity in wild type young mice (Tropea et al., 2006). We therefore tested if (1-3)

IGF-1 treatment could stabilize the prolonged OD plasticity observed in adult MeCP2 mutants. Female MeCP2+/− mice, aged P60 or more, were monocularly deprived for 4 days and treated concurrently with (1-3)IGF-1. FIG. 3C shows that (1-3)IGF-1 treatment prevented the OD plasticity in the adult Mecp2+/− mice, suggesting that indeed (1-3)IGF-1 rapidly induces synapse stabilization or maturation. Across all animals, ocular dominance plasticity was observed in young (P28) mice or adult (P60) MeCP2-deficient mice, but not in normal adult mice or MeCP2-deficient mice treated with (1-3)IGF-1 (FIG. 3D).

Bradycardia in MeCP2−/y Mice is Partially Rescued by (1-3) IGF-1 Treatment

In addition to examining the efficacy of (1-3)IGF-1 in ameliorating neurophysiological symptoms, we sought to characterize its effects on the general health of the organism. Clinical and experimental evidence shows autonomic system dysfunctions such as labile breathing rhythms and reduced baseline cardiac vagal tone in Rett Syndrome patients (Julu et al., 2001). A poor control of the feedback mechanisms that regulate blood pressure homeostasis through the sympathetic system, for example hyperventilation-induced decrease in heart rate, is common in Rett patients and can cause life threatening cardiac arrhythmias (Acampa and Guideri, 2006; Julu et al., 2001). The pathogenesis of the cardiac dysautonomia, although not well understood, suggests that immature neuronal connections in the brainstem could be the cause. To examine heart rate abnormalities in MeCP2−/y mice and the effect of (1-3)IGF-1 treatment, we monitored real time cardiac pulse rate in non-anesthetized wild type and MeCP2−/y animals treated with vehicle or (1-3)IGF-1. Wild type mice exhibited a regular distribution of heart rate measurements centered near 750 beats per minute (FIG. 4A). In contrast, MeCP2−/y mice exhibited a more irregular heart rate with a lower average rate, the occurrence of which was significantly reduced following treatment with (1-3)IGF-1.

(1-3)IGF-1 Administration Improves Locomotor Activity and Life Span

MeCP2−/y mice develop Rett-like symptoms beginning at 4-6 weeks of age when they progressively become lethargic, develop gait ataxia and die between 10 and 12 weeks of age (Chen et al., 2001). Baseline locomotor activity was thus also recorded in mice after 6 weeks by counting nocturnal infrared beam crossing events within a caged area (FIG. 4B). Here, MeCP2 knockout mice (KO) exhibited markedly reduced locomotor activity levels compared to wild-type mice (WT), but treatment with (1-3)IGF-1 (KO-T) elevated these levels. This elevation was specific to the knockout animals, with treatment failing to increase activity in wild-type animals (WT-T). These results are in contrast to those measured in younger animals (FIG. 6) in which no change in activity had been detected yet in the knockout mice, suggesting a phenotype that comes online with the developmental expression of the disease.

Finally, compared to MeCP2 KO littermates, MeCP2−/y mice treated with (1-3)IGF-1 also showed a ~50% increase in life expectancy (an increase in the 0.5 probability survival rate from ~60 days to 90 days).

We also measured the effect of (1-3)IGF1 treatment on neuron soma size in hippocampus. Mice were treated with (1-3)IGF1 as described above for locomotor activity. As shown in FIG. 7, soma size in neurons in the CA3 region of the hippocampus was significantly impaired in MeCP2 KO animals relative to wild-type animals. (1-3)IGF1 treatment increased average soma size in KO animals, but had no effect on soma size in wild type animals.

Discussion

In this study we provide evidence that (1-3)IGF-1 ameliorates symptoms of RTT in a mouse model of the disease. Several lines of evidence support the hypothesis that MeCP2 mutant animals display features of immature circuitry in the CNS that persist into adulthood. First, single neurons and synapses showed a reduction in excitatory postsynaptic currents, indicating immaturity or instability of synaptic contacts. Second, PSD-95, a marker of mature functional synapses and their strength, was down-regulated in MeCP2 null brains. Third, visual cortex connections in adult MeCP2+/− mice displayed synaptic changes following monocular deprivation usually characteristic of young mice. Systemic treatment of MeCP2 knockout mice with (1-3)IGF-1, which is known to stimulate IGF-1 signaling and mimic BDNF pathways in promoting neuronal and synaptic maturation, resulted in substantial improvement across the spectrum of these metrics, and also improved defects in heart rate, locomotor activity, and lifespan that were observed in the knockout.

Although these effects were highly significant, it is important to stress that MeCP2 knockout mice treated with (1-3) IGF-1 still develop the full range of symptoms and die prematurely. The disease progression in mice, like in patients, involves an almost asymptomatic early period followed by a progressive deterioration from 4 to 8 weeks with death occurring usually between 10 and 12 weeks. (1-3)IGF-1 treated mice develop symptoms at the same age as controls but live significantly longer and maintain increased activity during the later phase of the disease. IGF1 levels normally decrease with age, and artificially increasing levels of IGF-1 in rodents and humans has been associated with decreased muscle loss and improved mobility (Rudman et al., 1990). A similar effect might be mediated by (1-3)IGF-1 and might result in facilitated access of (1-3)IGF-1 treated mice to food and water. It is possible that (1-3)IGF-1 treatment also increases dendritic outgrowth or adult neurogenesis (Aberg et al., 2000; Aberg et al., 2003), and thus may contribute to the overall robustness and stabilization of signaling and circuitry. While no change was observed in the size of cell bodies as a result of the knockout or treatment, small changes were seen in the overall brain weight as a result of knockout and treatment.

Our results constitute the first functional evidence for the persistence of an immature state of cortical connections in the adult MeCP2+/− brain. Female MeCP2 mutant mice have an almost normal life span (8-10 months), and develop milder symptoms much later in life than male mutant mice. The pronounced effect on synaptic plasticity observed in the MeCP2 mutant female brain was, therefore, rather unexpected. Due to random X inactivation, approximately 50% of neurons in the brains of female MeCP2+/− mice express wild type MeCP2 protein. This would argue for a dominant effect of the mutant neurons on the entire synaptic network, consistent with the results of earlier genetic rescue experiments which demonstrated that reactivation of MeCP2 expression in >70% of the neurons did not prevent development of symptoms in MeCP2−/y mice (Giacometti et al., 2007). We speculate that (1-3)IGF-1 reduces OD plasticity in adult mutant mice by stabilizing synaptic contacts, though it might also increase the number of synaptic connections. It also appears that (1-3)IGF-1 acts rapidly in stabilizing synaptic contacts in the visual cortex, as the mice used for the monocular deprivation experiments were treated only for 4 days prior to the optical imaging. We cannot exclude the possibility that (1-3) IGF-1 affects non-neuronal cells; for example (1-3)IGF-1 treatment could increase vascular density and glucose utilization in the brain or have additional effects in peripheral tissues. In the experiments described, (1-3)IGF-1 was administered to the mice via intra-peritoneal injections. It is possible that other delivery methods, such as intravenous infusion or ventricular delivery would be more effective and potentially could further improve the extent of rescue of the symptoms.

In conclusion, we have shown that systemic delivery of (1-3)IGF-1 can significantly improve physiological behavior and survival in MeCP2 mutant mice. We also provide direct evidence that MeCP2 deficiency leads to immature synaptic function and organization which can be partially rescued by (1-3)IGF-1 administration, via a mechanism that could involve the PI3K/Akt/PSD-95 pathway. While further studies will be needed to unravel the exact mechanism of (1-3)IGF-1 action, the results presented here point to a potential utility of (1-3)IGF-1 and IGF1 signaling towards the treatment of Rett Syndrome. Successful therapies for RTT have significant implications for other autism spectrum disorders and neurodevelopmental disorders as well, given the significant overlap in phenotype, genetic susceptibility and proposed underlying neurobiological mechanisms.

Example 2

(1-3)IGF-1 Increases the Expression and Biological Activity of BDNF and tPA

The effect of (1-3)IGF-1 treatment on the expression and biological activity of BDNF and tPA during MD was examined. Mice were subjected to MD and treated with (1-3)IGF-1 as described above.

FIG. 8A shows the effects of (1-3)IGF-1 treatment on the expression levels of BDNF at the mRNA level. Monocular deprivation significantly decreased BDNF expression level in the contralateral V1. (1-3)IGF-1 treatment was able to increase expression in animals subjected to MD, though not to control levels.

FIG. 8B shows double staining for NeuN (green) and proBDNF (red) antibody. The protein expression confirms that (1-3)IGF-1 treatment was able to modulate the effects of MD by increasing BDNF protein expression, though not to control levels.

FIG. 8C shows the effects of (1-3)IGF-1 treatment on the mRNA expression levels of tPA at the mRNA level. (1-3) IGF-1 treatment significantly up-regulated tPA mRNA expression relative to both control and deprived animals.

FIG. 8D shows double staining for NeuN (red) and tPA (green) antibody. tPA staining, indicative of protein expression, was present in puncta in cell bodies and does not show prominent change in MD versus control. However, the expression level for tPA seems to be strongly increased by (1-3)IGF-1 treatment.

FIG. 8E represents a model of action of (1-3)IGF-1 on BDNF activation. (1-3)IGF-1 promotes BDNF activity both by directly affecting its expression and by controlling its biological activation through tPA (which is known to cleave pro BDNF into mature BDNF).

Example 3

IGF1 Exhibits Same Effects as (1-3)IGF-1

The above data focused on the (1-3)IGF-1 fragment of IGF1 to promote IGF1 signaling. We also have tested the effect of the full-length IGF1 peptide already approved for pediatric administration in human patients (for short stature indications). We have verified a correspondence in the effects of (1-3)IGF-1 and recombinant human IGF1 (rhIGF1). We measured effects on synaptic transmission during direct application of the two molecules, and found that they each succeeded comparably in eliciting striking enhancements of synaptic activity (FIG. 9A). Also, maturation of cortical circuitry during ocular dominance plasticity (i.e., as shown in Example 1) was promoted to similar degrees using either (1-3)IGF-1 or rhIGF1 (180 µg/kg/day delivered i.p. starting at 2 weeks, shown in FIG. 9B).

REFERENCES

Aberg, M. A., Aberg, N. D., Hedbacker, H., Oscarsson, J., and Eriksson, P. S. (2000). Peripheral infusion of IGF-I selectively induces neurogenesis in the adult rat hippocampus. J Neurosci 20, 2896-2903.

Aberg, M. A., Aberg, N. D., Palmer, T. D., Albom, A. M., Carlsson-Skwirut, C., Bang, P., Rosengren, L. E., Olsson, T., Gage, F. H., and Eriksson, P. S. (2003). IGF-I has a direct proliferative effect in adult hippocampal progenitor cells. Mol Cell Neurosci 24, 23-40.

Acampa, M., and Guideri, F. (2006). Cardiac disease and Rett syndrome. Arch Dis Child 91, 440-443.

Amir, R. E., Van den Veyver, I. B., Wan, M., Tran, C. Q., Francke, U., and Zoghbi, H. Y. (1999). Rett syndrome is caused by mutations in X-linked MECP2, encoding methyl-CpG-binding protein 2. Nat Genet 23, 185-188.

Baker, A. M., Batchelor, D. C., Thomas, G. B., Wen, J. Y., Rafiee, M., Lin, H., and Guan, J. (2005). Central penetration and stability of N-terminal tripeptide of insulin-like growth factor-I, glycine-proline-glutamate in adult rat. Neuropeptides 39, 81-87.

Bondy, C. A. (1991). Transient IGF-I gene expression during the maturation of functionally related central projection neurons. J Neurosci 11, 3442-3455.

Chahrour, M., and Zoghbi, H. Y. (2007). The story of rett syndrome: from clinic to neurobiology. Neuron 56, 422-437.

Chang, Q., Khare, G., Dani, V., Nelson, S., and Jaenisch, R. (2006). The disease progression of Mecp2 mutant mice is affected by the level of BDNF expression. Neuron 49, 341-348.

Chao, H. T., Zoghbi, H. Y., and Rosenmund, C. (2007). MeCP2 Controls Excitatory Synaptic Strength by Regulating Glutamatergic Synapse Number. Neuron 56, 58-65.

Chen, R. Z., Akbarian, S., Tudor, M., and Jaenisch, R. (2001). Deficiency of methyl-CpG binding protein-2 in CNS neurons results in a Rett-like phenotype in mice. Nat Genet 27, 327-331.

Chen, W. G., Chang, Q., Lin, Y., Meissner, A., West, A. E., Griffith, E. C., Jaenisch, R., and Greenberg, M. E. (2003). Derepression of BDNF transcription involves calcium-dependent phosphorylation of MeCP2. Science 302, 885-889.

Cohen, D. R., Matarazzo, V., Palmer, A. M., Tu, Y., Jeon, O. H., Pevsner, J., and Ronnett, G. V. (2003). Expression of MeCP2 in olfactory receptor neurons is developmentally regulated and occurs before synaptogenesis. Mol Cell Neurosci 22, 417-429.

Dani, V. S., Chang, Q., Maffei, A., Turrigiano, G. G., Jaenisch, R., and Nelson, S. B. (2005). Reduced cortical activity due to a shift in the balance between excitation and inhibition in a mouse model of Rett syndrome. Proc Natl Acad Sci USA 102, 12560-12565.

El-Husseini, A. E., Schnell, E., Chetkovich, D. M., Nicoll, R. A., and Bredt, D. S. (2000). PSD-95 involvement in maturation of excitatory synapses. Science 290, 1364-1368.

Gemelli, T., Berton, O., Nelson, E. D., Perrotti, L. I., Jaenisch, R., and Monteggia, L. M. (2006). Postnatal loss of methyl-CpG binding protein 2 in the forebrain is sufficient to mediate behavioral aspects of Rett syndrome in mice. Biol Psychiatry 59, 468-476.

Giacometti, E., Luikenhuis, S., Beard, C., and Jaenisch, R. (2007). Partial rescue of MeCP2 deficiency by postnatal activation of MeCP2. Proc Natl Acad Sci USA 104, 1931-1936.

Gordon, J. A., and Stryker, M. P. (1996). Experience-dependent plasticity of binocular responses in the primary visual cortex of the mouse. J Neurosci 16, 3274-3286.

Guan, J., Thomas, G. B., Lin, H., Mathai, S., Bachelor, D. C., George, S., and Gluckman, P. D. (2004). Neuroprotective effects of the N-terminal tripeptide of insulin-like growth factor-1, glycine-proline-glutamate (GPE) following intravenous infusion in hypoxic-ischemic adult rats. Neuropharmacology 47, 892-903.

Guy, J., Gan, J., Selfridge, J., Cobb, S., and Bird, A. (2007). Reversal of neurological defects in a mouse model of Rett syndrome. Science 315, 1143-1147.

Guy, J., Hendrich, B., Holmes, M., Martin, J. E., and Bird, A. (2001). A mouse Mecp2-null mutation causes neurological symptoms that mimic Rett syndrome. Nat Genet 27, 322-326.

Hofer, S. B., Mrsic-Flogel, T. D., Bonhoeffer, T., and Hubener, M. (2006). Prior experience enhances plasticity in adult visual cortex. Nat Neurosci 9, 127-132.

Itoh, M., Ide, S., Takashima, S., Kudo, S., Nomura, Y., Segawa, M., Kubota, T., Mori, H., Tanaka, S., Horie, H., et al. (2007). Methyl CpG-binding protein 2 (a mutation of which causes Rett syndrome) directly regulates insulin-like growth factor binding protein 3 in mouse and human brains. J Neuropathol Exp Neurol 66, 117-123.

Johnston, M. V., Jeon, O. H., Pevsner, J., Blue, M. E., and Naidu, S. (2001). Neurobiology of Rett syndrome: a genetic disorder of synapse development. Brain Dev 23 Suppl 1, S206-213.

Julu, P. O., Kerr, A. M., Apartopoulos, F., Al-Rawas, S., Engerstrom, I. W., Engerstrom, L., Jamal, G. A., and Hansen, S. (2001). Characterisation of breathing and associated central autonomic dysfunction in the Rett disorder. Arch Dis Child 85, 29-37.

Kaufmann, W. E., Taylor, C. V., Hohmann, C. F., Sanwal, I. B., and Naidu, S. (1997). Abnormalities in neuronal maturation in Rett syndrome neocortex: preliminary molecular correlates. Eur Child Adolesc Psychiatry 6 Suppl 1, 75-77.

Lee, C. C., Huang, C. C., Wu, M. Y., and Hsu, K. S. (2005). Insulin stimulates postsynaptic density-95 protein translation via the phosphoinositide 3-kinase-Akt-mammalian target of rapamycin signaling pathway. J Biol Chem 280, 18543-18550.

Liu, J. P., Baker, J., Perkins, A. S., Robertson, E. J., and Efstratiadis, A. (1993). Mice carrying null mutations of the genes encoding insulin-like growth factor I (Igf-1) and type 1 IGF receptor (Igf1r). Cell 75, 59-72.

Nan, X., Ng, H. H., Johnson, C. A., Laherty, C. D., Turner, B. M., Eisenman, R. N., and Bird, A. (1998). Transcriptional repression by the methyl-CpG-binding protein MeCP2 involves a histone deacetylase complex. Nature 393, 386-389.

Nelson, E. D., Kavalali, E. T., and Monteggia, L. M. (2006). MeCP2-dependent transcriptional repression regulates excitatory neurotransmission. Curr Biol 16, 710-716.

Ramsey, M. M., Adams, M. M., Ariwodola, O. J., Sonntag, W. E., and Weiner, J. L. (2005). Functional characterization of des-IGF-1 action at excitatory synapses in the CA1 region of rat hippocampus. J Neurophysiol 94, 247-254.

Riikonen, R., Makkonen, I., Vanhala, R., Turpeinen, U., Kuikka, J., and Kokki, H. (2006). Cerebrospinal fluid insulin-like growth factors IGF-1 and IGF-2 in infantile autism. Dev Med Child Neurol 48, 751-755.

Rudman, D., Feller, A. G., Nagraj, H. S., Gergans, G. A., Lalitha, P. Y., Goldberg, A. F., Schlenker, R. A., Cohn, L., Rudman, I. W., and Mattson, D. E. (1990). Effects of human growth hormone in men over 60 years old. N Engl J Med 323, 1-6.

Saura, J., Curatolo, L., Williams, C. E., Gatti, S., Benatti, L., Peeters, C., Guan, J., Dragunow, M., Post, C., Faull, R. L., et al. (1999). Neuroprotective effects of Gly-Pro-Glu, the N-terminal tripeptide of IGF-1, in the hippocampus in vitro. Neuroreport 10, 161-164.

Schuman, E. M. (1999). Neurotrophin regulation of synaptic transmission. Curr Opin Neurobiol 9, 105-109.

Shahbazian, M., Young, J., Yuva-Paylor, L., Spencer, C., Antalffy, B., Noebels, J., Armstrong, D., Paylor, R., and Zoghbi, H. (2002a). Mice with truncated MeCP2 recapitulate many Rett syndrome features and display hyperacetylation of histone H3. Neuron 35, 243-254.

Shahbazian, M. D., Antalffy, B., Armstrong, D. L., and Zoghbi, H. Y. (2002b). Insight into Rett syndrome: MeCP2 levels display tissue- and cell-specific differences and correlate with neuronal maturation. Hum Mol Genet 11, 115-124.

Sizonenko, S. V., Sirimanne, E. S., Williams, C. E., and Gluckman, P. D. (2001). Neuroprotective effects of the N-terminal tripeptide of IGF-1, glycine-proline-glutamate, in the immature rat brain after hypoxic-ischemic injury. Brain Res 922, 42-50.

Smith, S. L., and Trachtenberg, J. T. (2007). Experience-dependent binocular competition in the visual cortex begins at eye opening. Nat Neurosci 10, 370-375.

Tropea, D., Kreiman, G., Lyckman, A., Mukherjee, S., Yu, H., Horng, S., and Sur, M. (2006). Gene expression changes and molecular pathways mediating activity-dependent plasticity in visual cortex. Nat Neurosci 9, 660-668.

Tudor, M., Akbarian, S., Chen, R. Z., and Jaenisch, R. (2002). Transcriptional profiling of a mouse model for Rett syndrome reveals subtle transcriptional changes in the brain. Proc Natl Acad Sci USA 99, 15536-15541.

Xing, C., Yin, Y., Chang, R., Gong, X., He, X., and Xie, Z. (2007). Effects of insulin-like growth factor 1 on synaptic excitability in cultured rat hippocampal neurons. Exp Neurol 205, 222-229.

Yoshii, A., and Constantine-Paton, M. (2007). BDNF induces transport of PSD-95 to dendrites through PI3K-AKT signaling after NMDA receptor activation. Nat Neurosci 10, 702-711.

Zheng, W. H., and Quirion, R. (2004). Comparative signaling pathways of insulin-like growth factor-1 and brain-derived neurotrophic factor in hippocampal neurons and the role of the PI3 kinase pathway in cell survival. J Neurochem 89, 844-852.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

The entire contents of all of the references (including literature references, issued patents, published patent applications) cited throughout this application are hereby expressly incorporated by reference for the purpose cited herein.

The invention claimed is:

1. A method for treating Rett Syndrome characterized by methyl CpG-binding protein 2 (MeCP2) deficiency comprising
administering to a subject in need of such treatment an effective amount of insulin-like growth factor 1 (IGF1) and/or (1-3)IGF-1, to treat the subject.

2. The method of claim 1, wherein IGF1 is administered.

3. The method of claim 2, wherein the IGF1 is recombinant IGF1.

4. The method of claim 2, wherein the IGF1 is human IGF1.

5. The method of claim 2, wherein the dose of IGF1 administered is about 0.1-10 mg/kg/day.

6. The method of claim 5, wherein the dose of IGF1 administered is about 0.1-2 mg/kg/day.

7. The method of claim 1, wherein (1-3)IGF-1 is administered.

8. The method of claim 7, wherein the dose of (1-3)IGF-1 administered is about 0.1-100 mg/kg/day.

9. The method of claim 8, wherein the dose of (1-3)IGF-1 administered is about 6-20 mg/kg/day.

10. The method of claim 1, wherein the subject is a human.

11. The method of claim 1, wherein the IGF1 and/or (1-3)IGF-1 is administered orally, intravenously, intramuscularly, intranasally, intraperitoneally, subcutaneously, or intrathecally.

12. The method of claim 1, wherein the IGF1 and/or (1-3) IGF-1 is administered after diagnosis of Rett syndrome.

13. The method of claim 1, wherein the IGF1 and/or (1-3) IGF-1 is administered to the subject based on clinical diagnosis of Rett syndrome prior to confirmation of MeCP2 deficiency.

14. The method of claim 1, wherein the subject is free of symptoms otherwise calling for treatment with the IGF1 and/or (1-3)IGF-1.

15. The method of claim 1, further comprising first testing the subject for a mutation in a gene coding for methyl CpG-binding protein 2 (MeCP2).

16. The method of claim 1, further comprising administering to the subject tPA, BDNF, or a benzodiazepine and wherein the tPA, BDNF or benzodiazepine and the IGF1 and/or (1-3)IGF-1 are administered in a combined amount effective to treat the subject.

17. The method of claim 1, wherein the amount of IGF1 and/or (1-3)IGF-1 is effective to restore synaptic function and/or maturation, consolidate synapses and/or regulate neuronal plasticity.

18. The method of claim 1, wherein the IGF1 and/or (1-3) IGF-1 is administered as a pharmaceutical composition.

19. The method of claim 18, pharmaceutical composition comprises IGF1 and/or (1-3)IGF-1 combined with a stabilizing agent or carrier.

20. The method of claim 19, wherein the stabilizing agent or carrier is a polyethylene glycol.

* * * * *